United States Patent [19]

Sugama et al.

[11] Patent Number: 5,326,450
[45] Date of Patent: Jul. 5, 1994

[54] MINIATURIZED OXYGEN ELECTRODE

[75] Inventors: Akio Sugama; Hiroaki Suzuki; Naomi Kojima, all of Kawasaki, Japan

[73] Assignee: Fujitsu Limited, Kawasaki, Japan

[21] Appl. No.: 987,163

[22] Filed: Dec. 8, 1992

Related U.S. Application Data

[63] Continuation-in-part of Ser. No. 850,834, Mar. 13, 1992, Pat. No. 5,281,323.

[30] Foreign Application Priority Data

| Mar. 20, 1991 | [JP] | Japan | 3-057220 |
| May 28, 1991 | [JP] | Japan | 3-123787 |
| Oct. 26, 1992 | [JP] | Japan | 4-287618 |

[51] Int. Cl.$^5$ .......................................... G01N 27/26
[52] U.S. Cl. .................................. 204/415; 204/403; 204/412; 204/414; 204/416
[58] Field of Search ........... 204/403, 414, 415, 153.17, 204/412, 416

[56] References Cited

U.S. PATENT DOCUMENTS

| 4,001,042 | 1/1977 | Trocciola et al. | 427/115 |
| 4,874,500 | 10/1989 | Madou et al. | 204/412 |
| 4,975,175 | 12/1990 | Karube et al. | 204/403 |

FOREIGN PATENT DOCUMENTS

| 0030503 | 6/1981 | European Pat. Off. |
| 0100667 | 2/1984 | European Pat. Off. |
| 284518 | 9/1988 | European Pat. Off. |
| 2-236154 | 9/1990 | Japan |
| 2-240556 | 9/1990 | Japan |

OTHER PUBLICATIONS

Inspec Database Abstract No. A86097437, Institute of Electrical Engineers, London, GB; S. J. Pace et al.: "A Thick-Film Multi-Layered Oxygen Sensor" and Transducers '85-1985 International Conference on Solid State Sensors and Actuators Digest of Technical Papers (Cat. No. 85 CH2127-9) 1985, IEEE, New York, N.Y., pp. 406-409.
World Patents Index Latest Derwent Publications Ltd., London, GB; Database WPIL, Accession No. 90-330569, week 9044; and JP-A-2 236154 (Fujitsu) Aug. 19, 1990.
Patent Abstracts of Japan, vol. 14, No. 554 (P-1140), Mar. 9, 1989 and JP-A-2 236154 (Fujitsu) Aug. 19, 1990.
C. S. Cha et al.: "Problems Associated with the Miniaturization of a Voltammetric Oxygen Sensor: Chemical Crosstalk Among Electrodes," Sensors and Actuators B. 2 (0925-4005/90), 1990, pp. 239-242.
Patent Abstracts of Japan, vol. 11, No. 223 (P-597), Jul. 21, 1987 (JP 62-039755, Feb. 20, 1987).

Primary Examiner—John Niebling
Assistant Examiner—Bruce F. Bell
Attorney, Agent, or Firm—Staas & Halsey

[57] ABSTRACT

A miniaturized oxygen electrode which comprises: an electrically insulating substrate; an electrolyte-containing material disposed on the substrate and capable of serving as an electrolytic solution when supplied with water; a set of component electrodes disposed on the substrate and composed of a first component electrode on which a reduction reaction of oxygen dissolved in the electrolytic solution occurs when the miniaturized oxygen electrode is operated and one or more second component electrodes other than the first component electrode, the first component electrode being interconnected with the second component electrodes through the electrolyte-containing material; an oxygen gas-permeable membrane covering the electrolyte-containing material; and the electrolyte-containing material having a length for providing a sufficient distance along the interconnection between the first and second component electrodes such that any electroactive substances, formed on one of the first and second component electrodes during the operation of the miniaturized oxygen electrode, are prevented from reaching the other of the first and second component electrodes when diffusing along the length of the electrolytic solution.

14 Claims, 52 Drawing Sheets

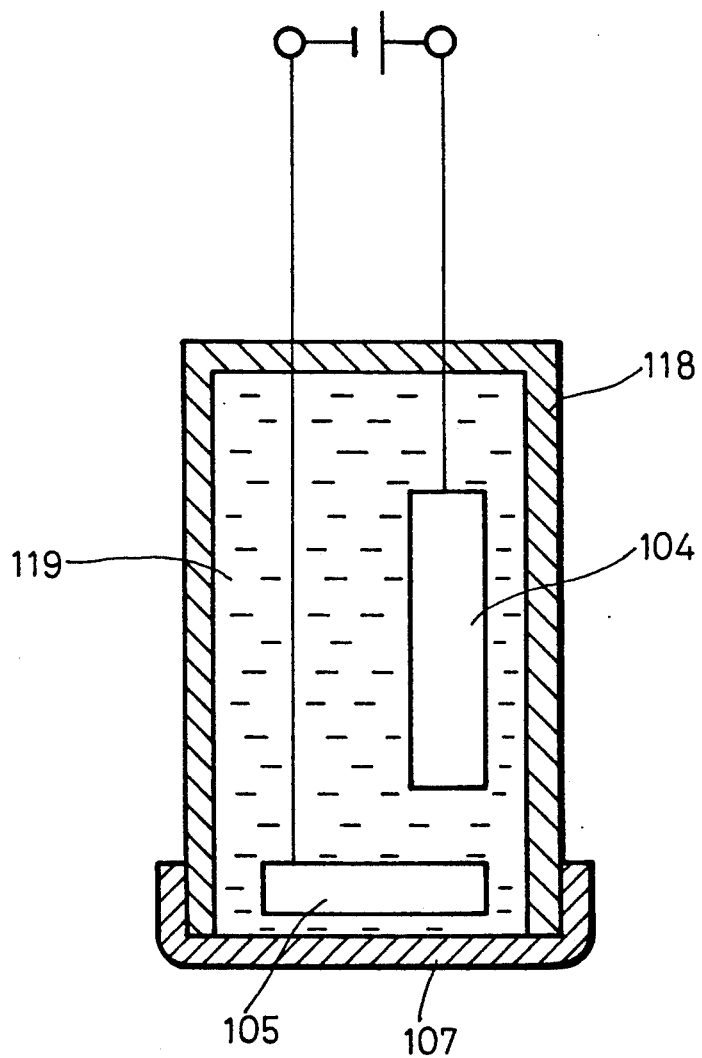

(PART OF SECTION TAKEN ALONG LINE I-I OF Fig.2(a))

I-I SECTION

PLAN VIEW

I-I SECTION

PLAN VIEW

I-I SECTION

PLAN VIEW

I-I SECTION

PLAN VIEW

I-I SECTION

PLAN VIEW

PLAN VIEW (ENTIRE WAFER)

I-I SECTION

PLAN VIEW (ENTIRE WAFER)

I-I SECTION

PLAN VIEW (ENTIRE WAFER)

I-I SECTION

PLAN VIEW (ENTIRE WAFER)

(PART OF SECTION TAKEN ALONG LINE I-I OF Fig.8(a))

I-I SECTION

PLAN VIEW

I-I SECTION

PLAN VIEW

I-I SECTION

PLAN VIEW

I-I SECTION

PLAN VIEW

I-I SECTION

PLAN VIEW

Fig.13A
Fig.13B
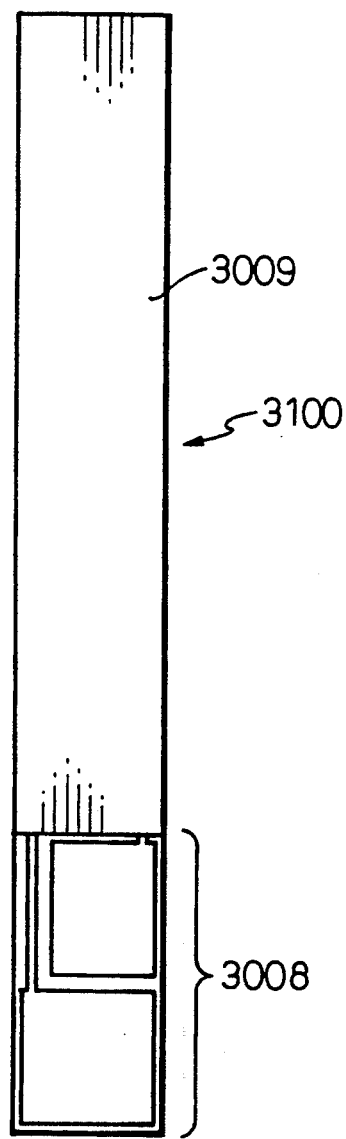
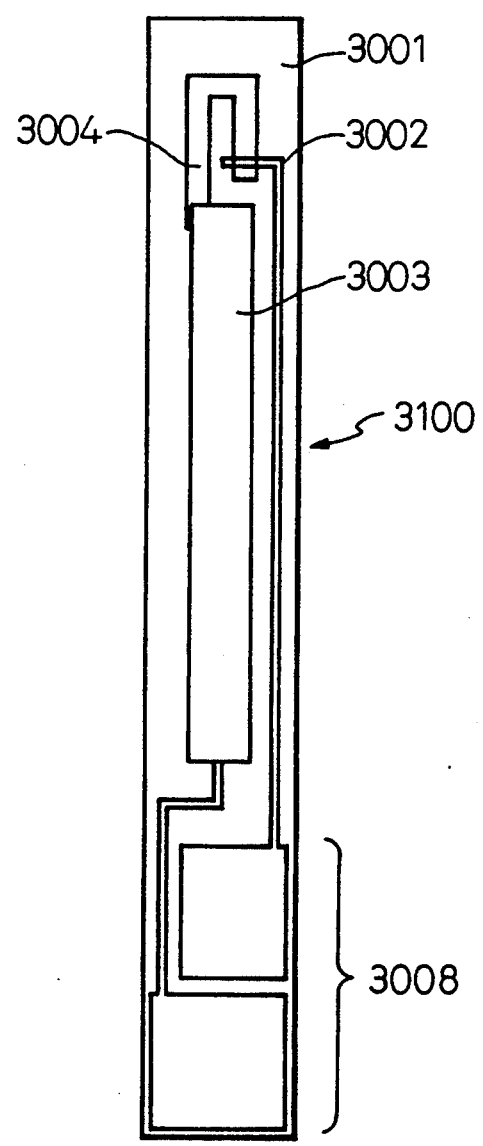

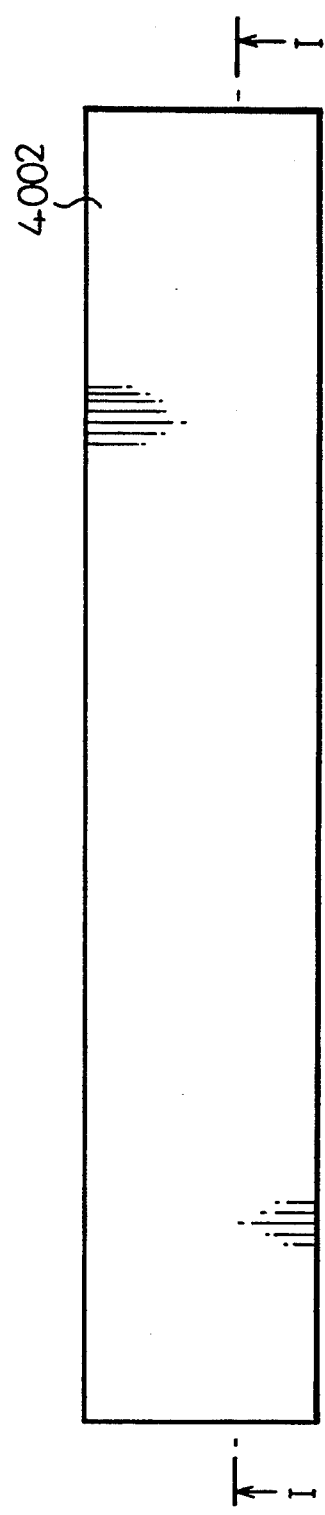
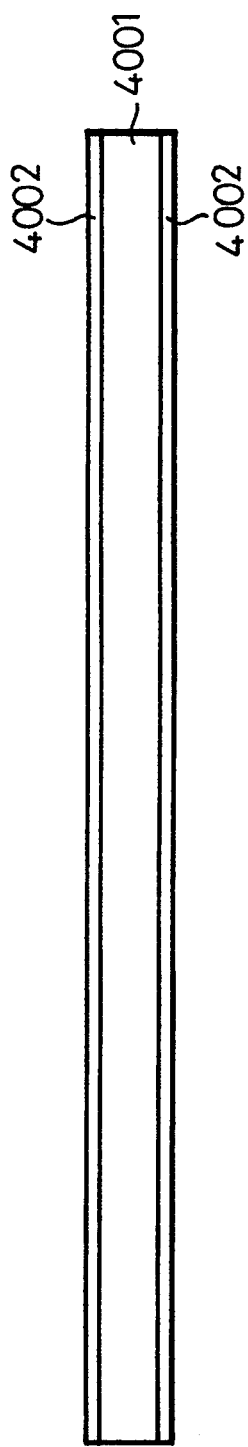
Fig.14A(a)　Fig.14A(b)

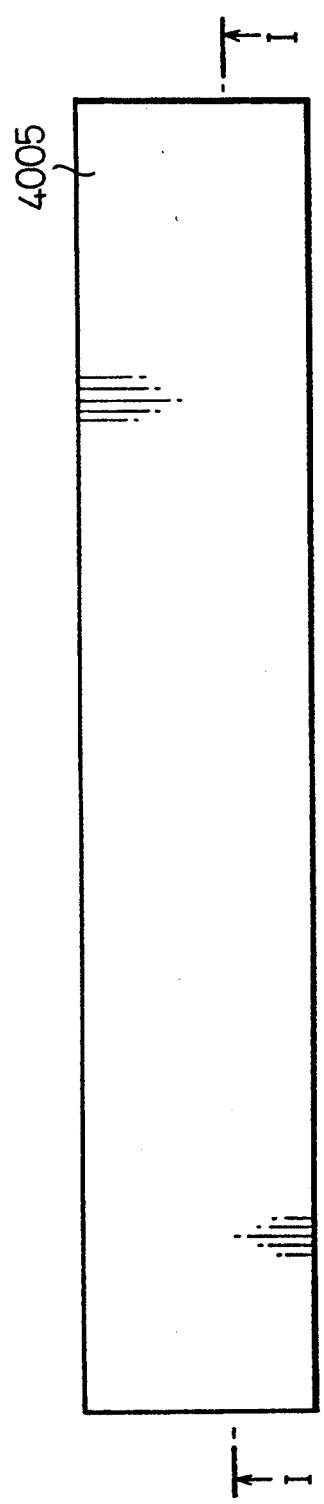
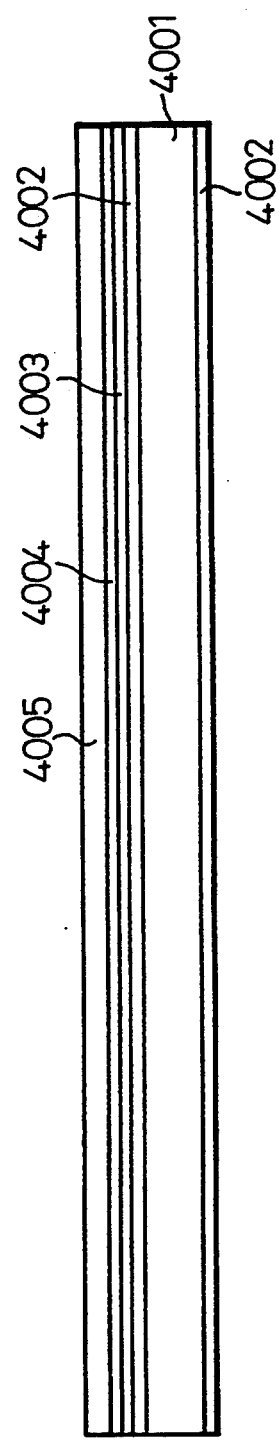
Fig.14B(a)
Fig.14B(b)

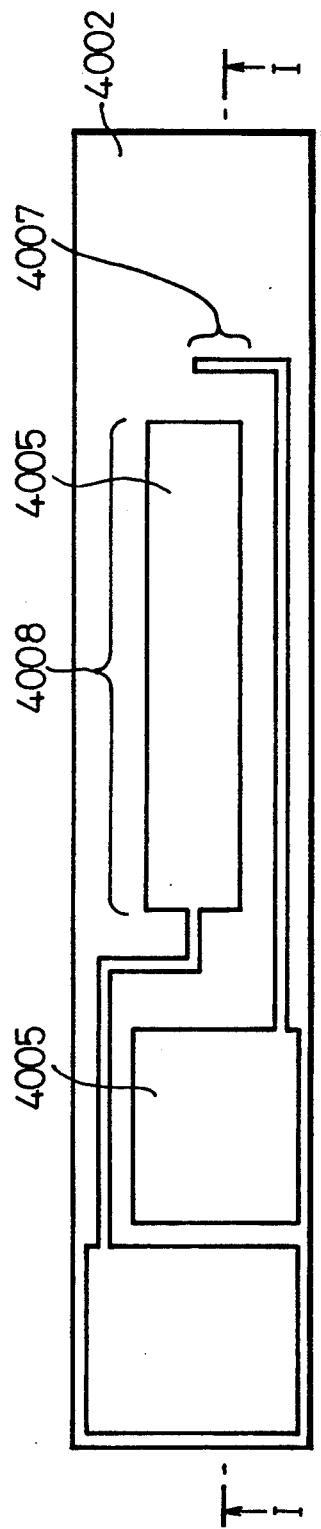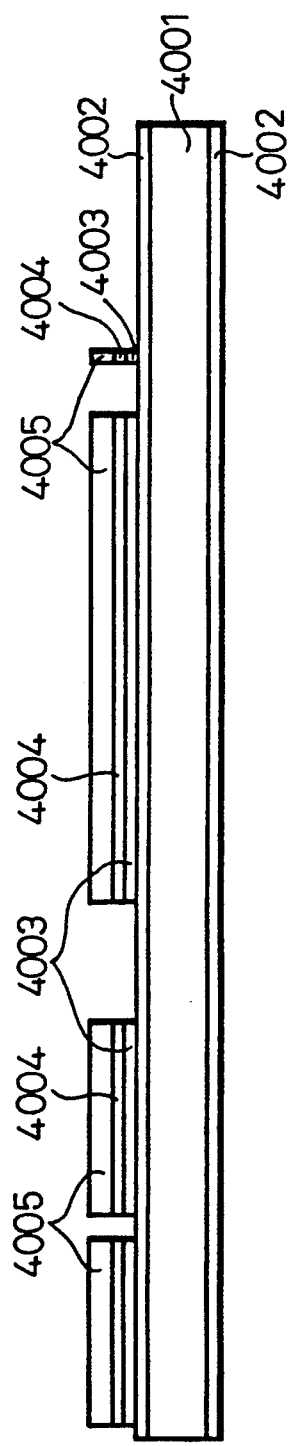
Fig.14D(a)
Fig.14D(b)

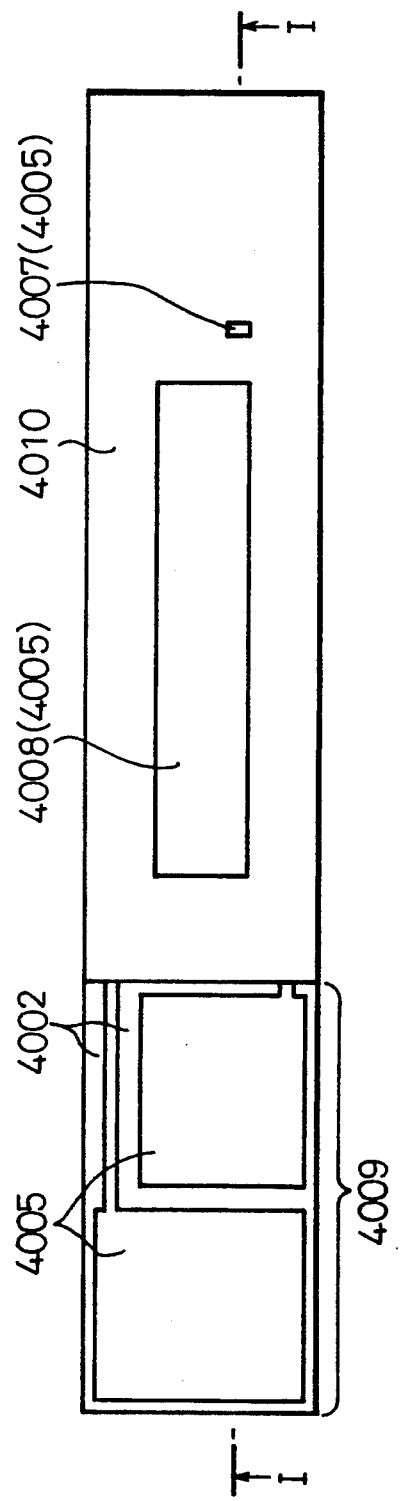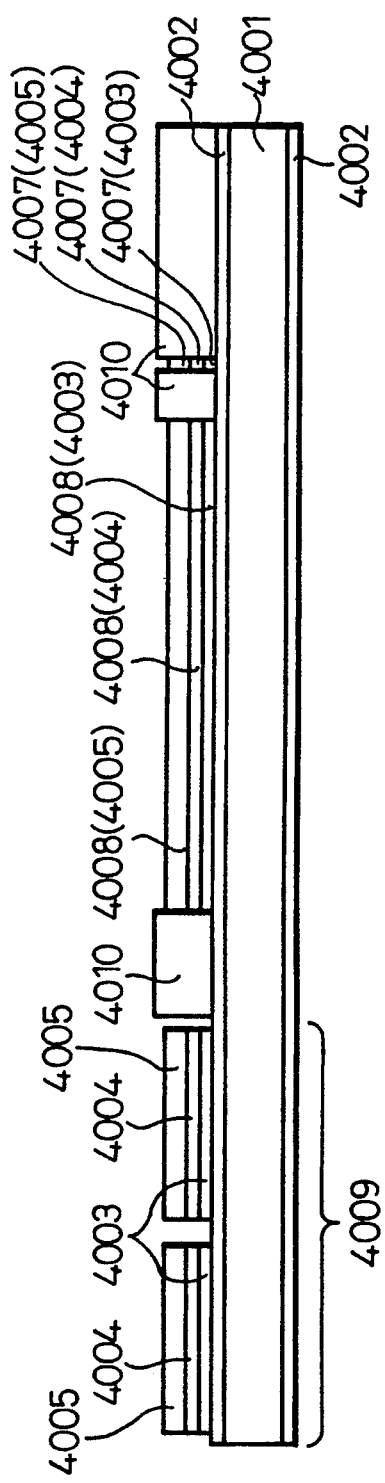

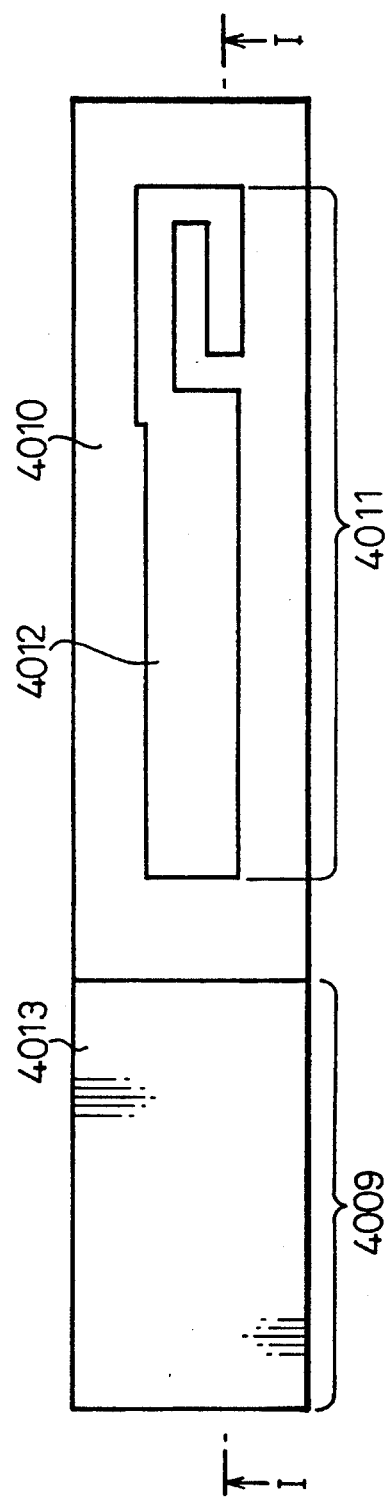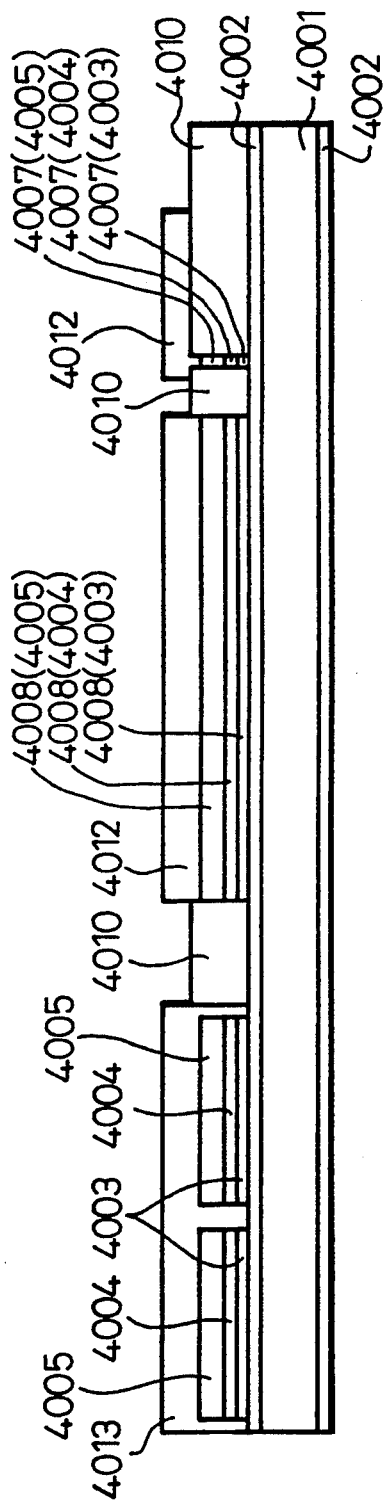
Fig.14G(a)
Fig.14G(b)

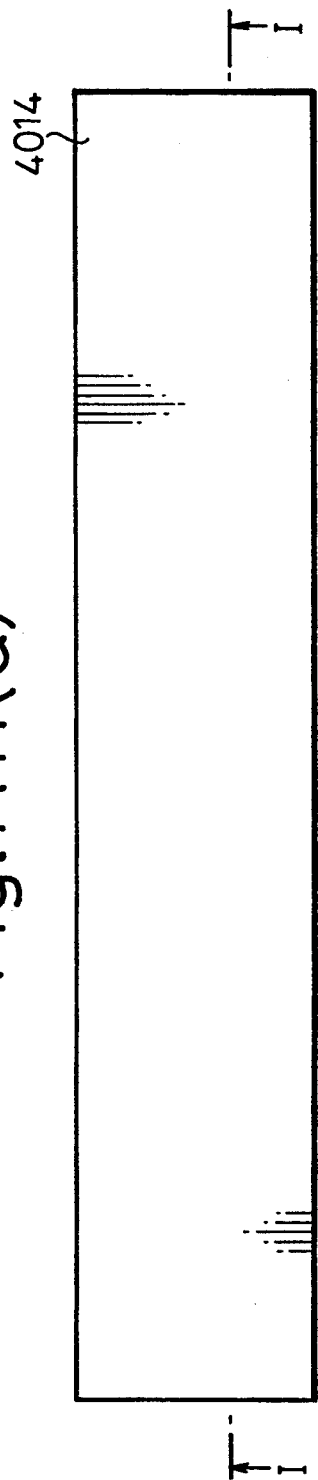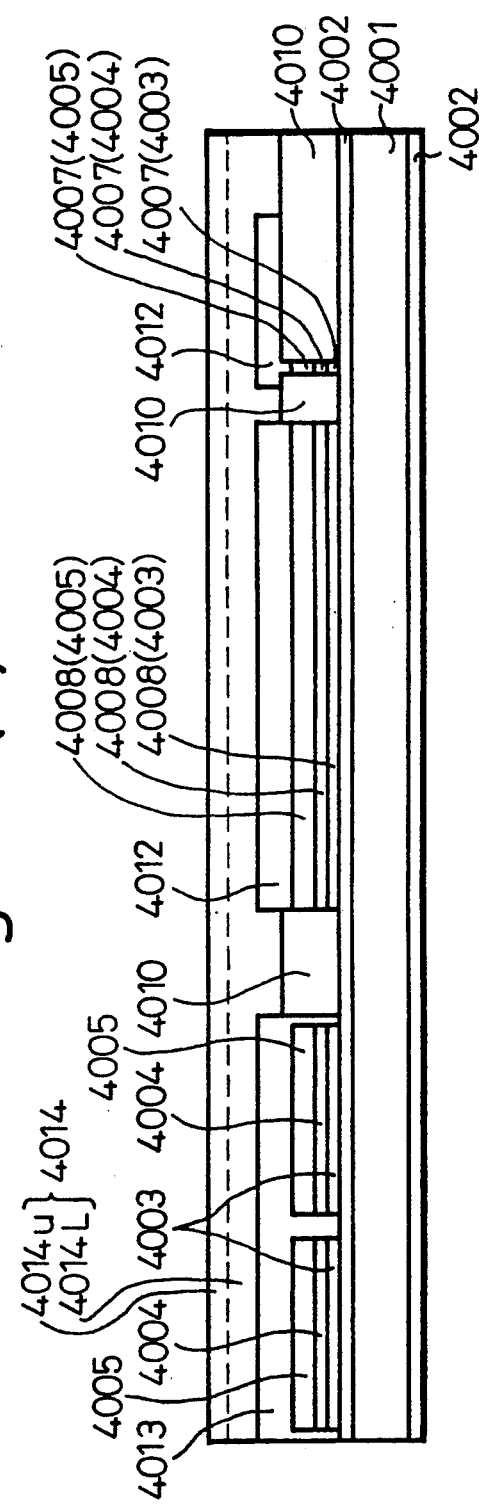

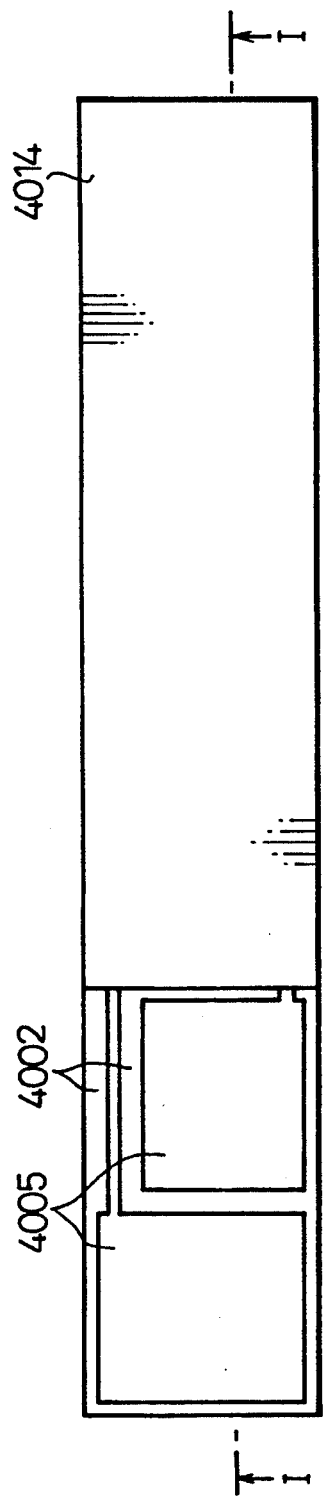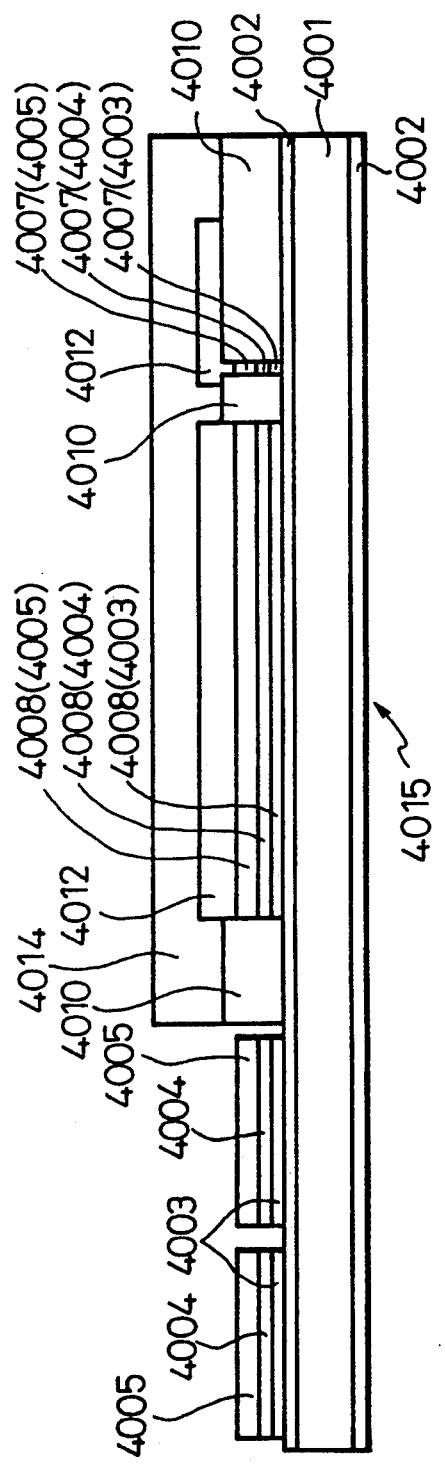

Fig.15A
Fig.15B
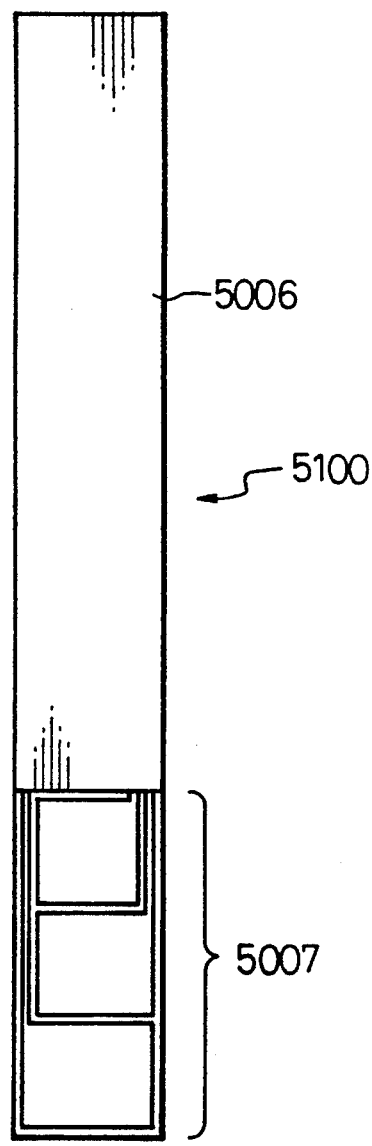
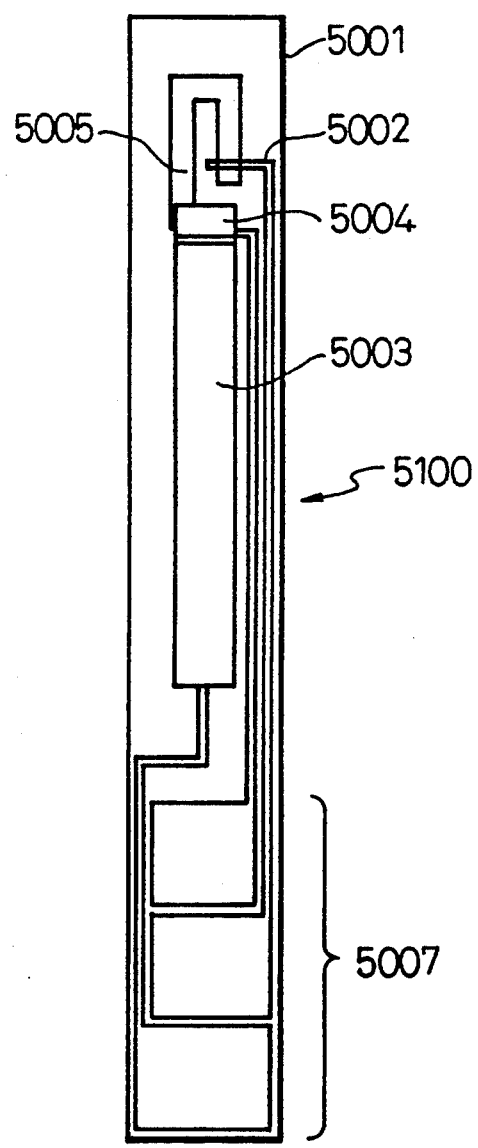

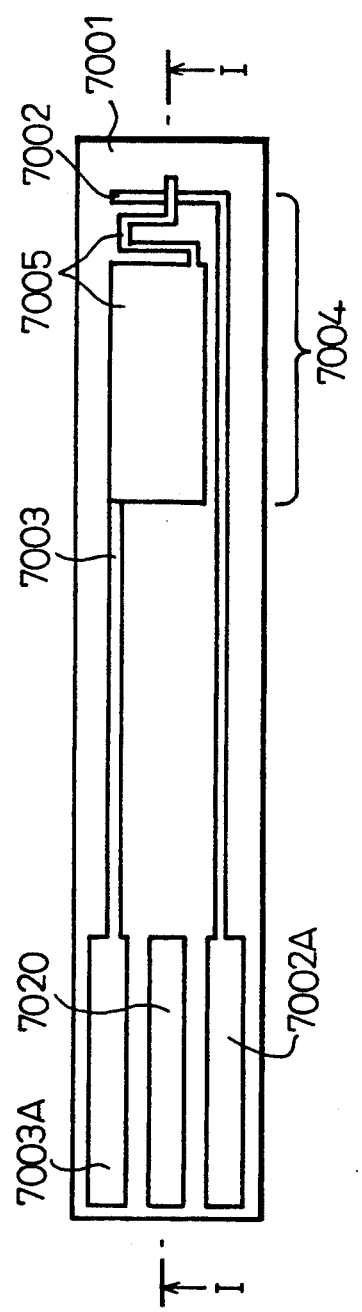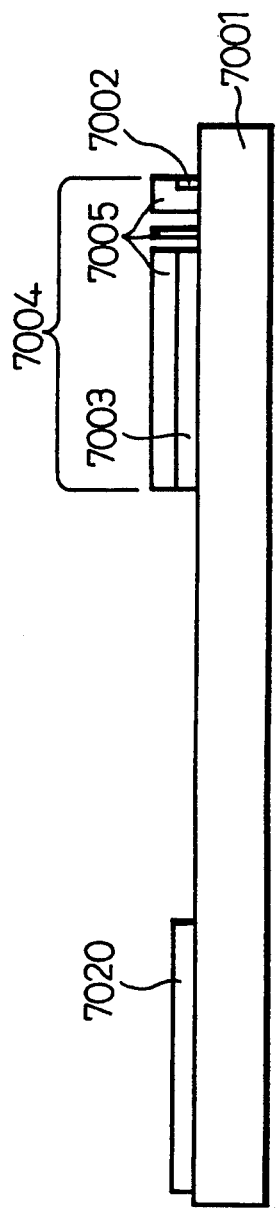

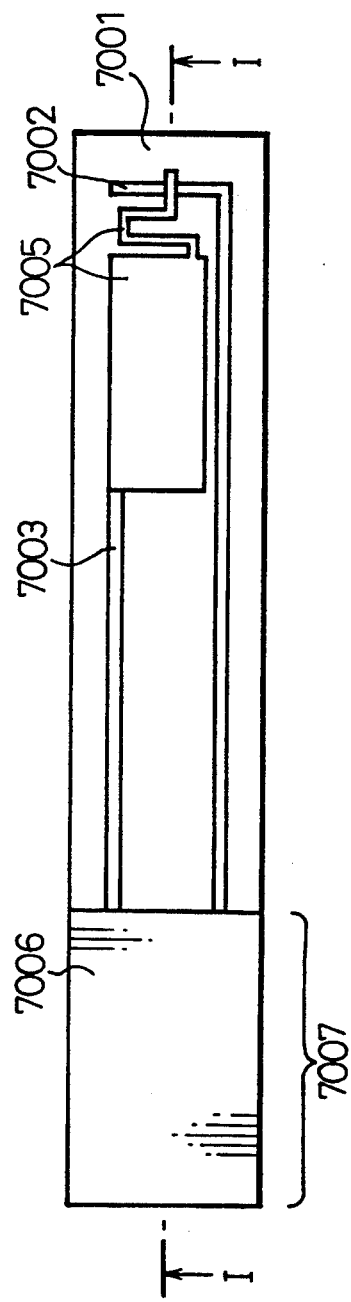
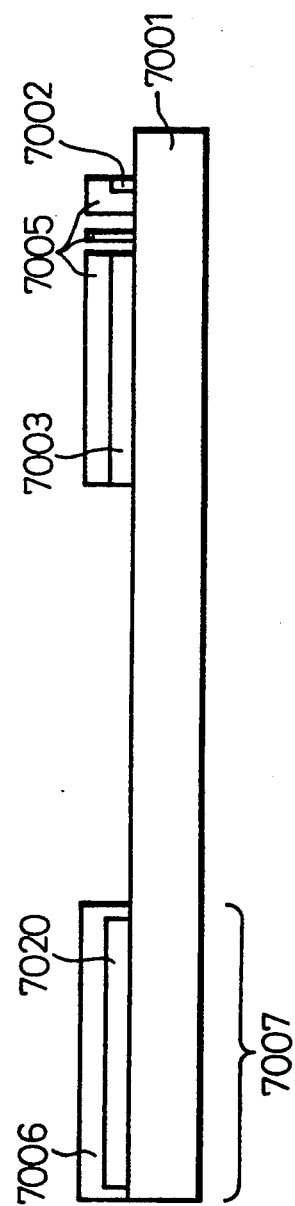

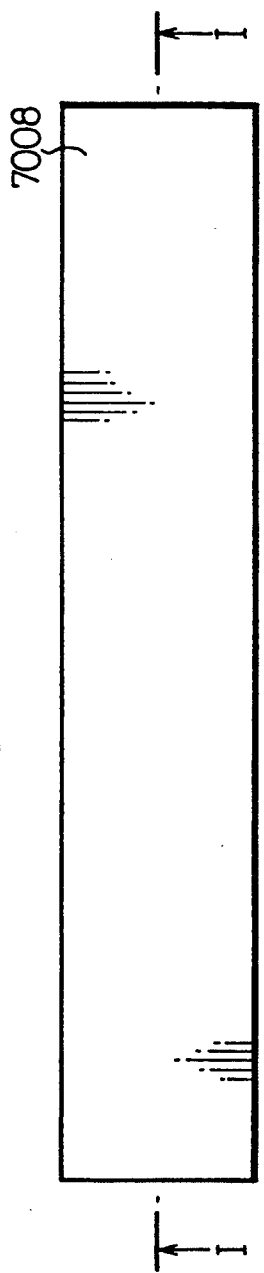
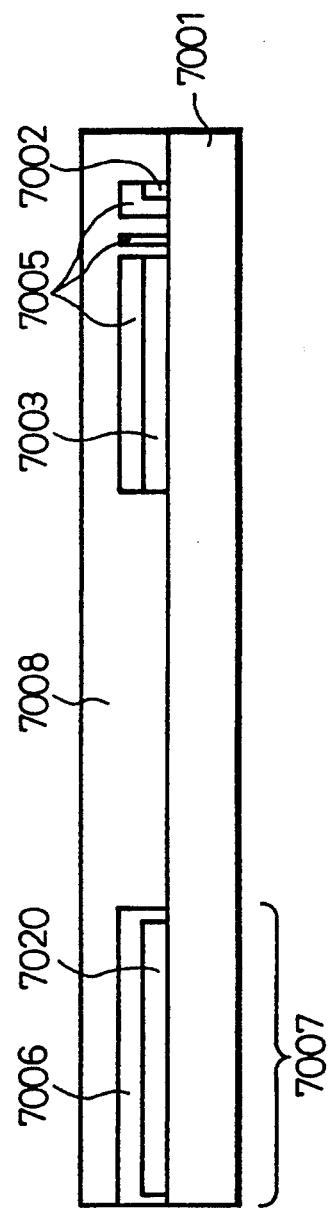

MINIATURIZED OXYGEN ELECTRODE

CROSS-REFERENCES TO RELATED APPLICATIONS

This application is a continuation-in-part application of U.S. Ser. No. 07/850,834 filed on Mar. 13, 1992, now U.S. Pat. No. 5,281,323.

BACKGROUND OF THE INVENTION

1. Field of the Invention

The present invention relates to a diaphragm-type miniaturized oxygen electrode, more particularly, to a miniaturized oxygen electrode useful for many applications including a measurement of the dissolved oxygen concentration of a solution, to an electrolyte composition suitable for forming the sensing site of the miniaturized oxygen electrode, and to a process of mass-producing miniaturized oxygen electrodes having a uniform quality.

An oxygen electrode is very useful for measuring the dissolved oxygen concentration in many fields. For example, oxygen electrodes are used in the field of water control, the BOD (Biochemical Oxygen Demand) in water is measured, and in the fermentation and brewing field, the dissolved oxygen concentration of a fermentation tank or fermenter is measured, to ensure an efficient fermentation of alcohol, etc.

An oxygen electrode can be combined with an enzyme to form a biosensor or an enzyme electrode to be used for measuring the concentration of sugar, vitamins, etc. For example, an oxygen electrode can be combined with glucose oxidase to measure the concentration of glucose or grape sugar. This utilizes a phenomenon in which glucose is oxidized by the dissolved oxygen with the aid of a catalytic action of glucose oxidase to form gluconolactone, with a resulting reduction of the dissolved oxygen amount diffusing into an oxygen electrode.

In addition to the measurement of the dissolved oxygen concentration of a solution, an oxygen electrode can be advantageously used for controlling the oxygen concentration of a gas phase. For example, a reduction of the ambient oxygen concentration to below 18% causes a dangerous oxygen deficiency, and in medical-care equipment, such as oxygen inhalation and gas anesthetization, the oxygen concentration of a gas used must be strictly controlled.

The oxygen electrode is thus very advantageously used in many fields, including environmental instrumentation, the fermentation industry, clinical care, and industrial hygiene.

2. Description of the Related Art

The conventional oxygen electrode typically has a structure as shown in FIG. 1, wherein a vessel or container 118 made of glass, plastics, stainless steel, or the like has an open end (lower end) covered and sealed with an oxygen gas-permeable membrane 107 made of silicone resin, fluororesin or the like, and an aqueous solution 119 of potassium chloride (KCl), sodium hydroxide (NaOH), etc., is filled in the vessel 118, in which an anode 104 made of silver (Ag), lead (Pb), etc., and a cathode 105 made of platinum (Pt), gold (Au), etc., are arranged.

The conventional oxygen electrode has a complicated structure, and therefore, it is difficult not only to miniaturize but also to mass-produce same.

The present inventors and others have proposed a new type of miniaturized oxygen electrode that can be produced by utilizing a semiconductor production process including a photolithography and an anisotropic etching, as disclosed in Japanese Unexamined Patent Publication (Kokai) No. 63-238,548 and U.S. Pat. No. 4,975,175.

The proposed oxygen electrode has a structure as shown in FIGS. 2 and 3, in which FIG. 2(b) shows an unfinished structure in which an oxygen gas-permeable membrane is not yet formed. This structure is produced by the following sequence. Two grooves 202 to be filled with an electrolyte-containing material are formed on a silicon wafer 201 by an anisotropic etching and the wafer surface is then covered by an $SiO_2$ insulating layer 203 to form an electrically insulating substrate. Then, two component electrodes, i.e., an anode 204 and a cathode 205, are formed on the insulating layer 203. The anode 204 has one end 204A for external electrical connection and the other end of two branches extending into the grooves 202. The cathode 205 has one end 205A for external electrical connection and the other end extending to the top surface of a plateau retained between the grooves 202. An electrolyte-containing material 206 is filled in the grooves 202, and the filled electrolyte-containing material 206 is in contact with the anode 204 within the grooves 202 and with the cathode 205 on the plateau. The upper surface of the filled electrolyte-containing material 206 is then covered with an oxygen gas-permeable membrane 207.

Nevertheless, the step of filling the grooves 202 with the electrolyte-containing material 206 and the step of covering the filled electrolyte-containing material 206 with the oxygen gas-permeable membrane 207 are difficult to carry out in a semiconductor process, and therefore, are manually carried out chip by chip after the wafer 201 on which miniaturized oxygen electrodes have been formed is cut into chips forming respective oxygen electrodes. The manual operation is a serious obstacle to the realizing of a mass-production, and further, involves too much fluctuation in operation to obtain miniaturized oxygen electrodes having a stable or uniform performance.

Therefore, it has been desired to provide a structure of a miniaturized oxygen electrode and a production process thereof in which the filling of an electrolyte-containing material and the forming of an oxygen gas-permeable membrane can be carried out collectively or generally and uniformly, on a wafer as a whole, before the wafer is cut into chips.

The step of filling an electrolyte-containing material has the following problems.

The present inventors studied gels containing an aqueous solution of potassium chloride and polyelectrolytes and found that, because many of these are not photosensitive, the photolithography used in the semiconductor process cannot be actually applied to the filling of an electrolyte-containing material.

The electrolyte-containing material must be a liquid having a fluidity when it is filled in a groove, and the filled material must form a dense film after being dried. Also, whether or not the filled material contains water significantly affects the quality of an oxygen gas-permeable membrane applied on the filled material, and therefore, upon application for an oxygen gas-permeable membrane, the electrolyte-containing material is preferably dried. The water required for the measurement of the oxygen concentration is supplied as a water vapor through the gas-permeable membrane just before the measurement starts. The electrolyte-containing material need not contain water during the production of an oxygen electrode.

Screen printing is a preferred method of filling an electrolyte-containing material collectively in a number of miniaturized oxygen electrodes on a wafer. This screen printing generally uses an emulsion mask and a metal mask to define a printed pattern. An emulsion mask is prepared by applying a photosensitive resin in the form of an emulsion on a mesh of a stainless steel, etc. to provide a printing pattern. Some resins have a transparency which advantageously facilitates the fine alignment required when producing a miniaturized oxygen electrode because a wafer covered by a resin mask is visible through the resin. The emulsion mask, however, is very weak against water, as can be understood from the fact that the developing treatment of an emulsion is carried out by using water, and the printing of a water-containing substance is difficult. On the other hand, the metal mask is prepared by forming holes in a plate of a stainless steel, etc., and therefore, is strong against water. The metal mask, however, is disadvantageous for the fine alignment, because it does not have a transparency. Moreover, the metal mask occasionally provides a printing quality lower than that obtained by the emulsion mask, when using some kinds of printing inks.

The present inventors proposed a process in which an electrolyte-containing gel is applied by screen printing, i.e. calcium alginate gel, polyacrylamide gel, and agarose gel are printed, as disclosed in Japanese Unexamined Patent Publication (Kokai) No. 1-56,902. This process uses a metal mask to print an aqueous gel and cannot be advantageously used in the production of a miniaturized oxygen electrode, for the reasons mentioned above. Moreover, a strong film cannot be obtained because an oxygen gas-permeable membrane is formed on a wet gel.

Potassium chloride is generally used as the electrolyte of an oxygen electrode. Although potassium chloride is a superior electrolyte, it is not suitable for use in a miniaturized oxygen electrode because it has a drawback in that it is only soluble in water and that a filled aqueous solution becomes a white brittle powder when dried. The present inventors also proposed a polyelectrolyte, as disclosed in Japanese Unexamined Patent Publication (Kokai) No. 2-240,556. Although this has a good film forming property, the proposed polyelectrolyte is also soluble only in water, and is difficult to treat because it has a high polymerization degree and exhibits a high viscosity even as a dilute solution.

The step of forming an oxygen gas-permeable membrane has the following problems.

The gas-permeable membrane is made of silicone resin, fluororesin, or other electrically insulating material. The gas-permeable membrane is therefore formed not to cover the whole surface of a wafer but to have a pattern such that the component electrode ends or "pads" 204A and 205 for external electrical connection are exposed. The gas-permeable membrane is formed selectively in the predetermined wafer region other than the pad region to be exposed either by applying a resin only to the predetermined region or by first forming the gas-permeable membrane on the whole surface of a wafer and then removing the gas-permeable membrane in the pad region to be exposed.

A screen printing of a liquid resin is known as the former method, i.e., the selective application of a resin. This method has an advantage in that a single printing operation simultaneously effects both the application and the patterning of a resin, but the silicone resin used for forming a gas-permeable membrane is progressively cured by the water in the ambient air, and therefore, the viscosity of the resin varies during printing to cause a nonuniform printing, and in the worst case, a clogging of a printing stencil.

A lift-off process using a photoresist is known as the latter method, i.e., the formation and selective removal of a gas-permeable membrane. This process has an advantage in that the semiconductor process is advantageously applied and a complicated pattern can be easily obtained. This method, however, when applied in the production of a miniaturized oxygen electrode, provides a completely cured gas-permeable membrane having a high strength such that the membrane is difficult to peel or exfoliate selectively at the portion to be exposed, even by using an ultrasonic treatment. Thus, the lift-off process cannot be practically used in the production of a miniaturized oxygen electrode.

U.S. Pat. No. 4,062,750 to J.F. Butler discloses a thin film type electrochemical electrode formed on a silicon substrate, having a feature in that an electroconductive layer extends through the silicon substrate thickness so that a signal from a sensor disposed on one side of the substrate is taken out from the other side of the substrate. As this electrode does not have the pad portion of the present inventive electrode, a gas-permeable membrane may cover the whole surface and a patterning of the membrane for exposing the pad portion is not required. This electrode, however, requires a complicated production process, causing a problem in the practical application. The filling of an electrolyte is carried out by vacuum deposition, and although sodium chloride and potassium chloride can be vacuum deposited, many of the inorganic salts used as a buffering agent are deteriorated by dehydration and condensation when exposed to the heat associated with vacuum deposition. Therefore, even when a buffered electrolyte is obtained, the resulting pH will significantly deviate from an expected value and the obtained electrolyte composition must be very restricted, and thus this is not an optimum process. Moreover, problem arises when a single vacuum deposition apparatus is used for both depositing electrolytes and for depositing electrode metals, and therefore, individual deposition apparatuses must be provided for the respective depositions.

M.J. Madou et al. proposed a microelectrochemical sensor, as disclosed in U.S. Pat. No. 4,874,500 and in AIChE SYMPOSIUM SERIES, No. 267, vol. 85, pp. 7–13 (1989). This sensor also has a feature in that an electroconductive layer extends through the silicon substrate thickness and a signal from a sensor disposed on one side of the substrate is taken out from the other side of the substrate, and therefore, has the same drawback as that of J.F. Butler. An electrolyte is filled in such a manner that an alcoholic solution of poly(hydroxyethylmathacrylate), etc. is painted on, the solvent is evaporated, an electrolyte solution is introduced to form a gel, and then dried. The conventional problem is apparently eliminated, because an electrolyte is introduced after a polymer is applied, but a crystal grows when a potassium chloride solution is evaporated. When the amount of potassium chloride is small, the grown crystal is enclosed with the polymer, but when the amount is large, a number of large crystals appear, which may not be supported by the polymer. On the other hand, the amount of an electrolyte must be as large as possible, because the service life of an oxygen electrode is affected by the electrolyte amount contained therein. Thus, the restricted amount of electrolyte reduces the service life of an oxygen electrode.

A typical arrangement of the conventional oxygen electrode shown in FIG. 1, usually referred to as a "Clark type oxygen electrode", has an electrolytic solution 119 composed of an aqueous solution of potassium chloride (KCl) and an anode 104 made of silver. In this arrangement, an application of voltage across the cathode 105 and the anode 104 causes the following reactions:

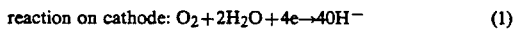

reaction on cathode: $O_2 + 2H_2O + 4e \rightarrow 4OH^-$ (1)

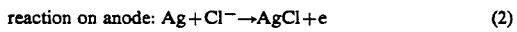

reaction on anode: $Ag + Cl^- \rightarrow AgCl + e$ (2)

Oxygen of a measuring object is dissolved in the electrolytic solution, reduced on the cathode and measured in terms of a current corresponding to the amount of oxygen reduced. On the anode, the silver of the anode and the chloride ions of the electrolytic solution react (or oxidation of silver occurs) to form silver chloride and thereby are consumed.

Thus, to ensure a long period of operation of an oxygen electrode, the silver and the potassium chloride must be present in a sufficient amount.

The Clark type oxygen electrode such as shown in FIG. 1 has at least the size of a pencil and can easily contain a large amount of silver and electrolytic solution.

On the other hand, the miniaturized oxygen electrode of the present invention is as minute as some square millimeters and does not have a large volume for containing the consumable substances including the anode material such as silver and the electrolyte components such as chloride ions, for example, of KCl. Thus, the miniaturized oxygen electrode is made with an increased anode thickness and an increased concentration of the electrolyte components, to ensure the necessary amount thereof for a long period of operation.

Under normal conditions, the silver chloride formed on the anode is hard to dissolve in water and deposits on the anode, but under an increased concentration of chloride ions, the silver chloride reacts with the chloride ions to form a water-soluble complex, which is dissolved in the electrolytic solution, diffuses into the cathode and is reduced there. This means that a reducing reaction other than the reduction of oxygen as expressed by the formula (1) occurs on the cathode, and therefore, the oxygen electrode does not provide an accurate output current corresponding to the oxygen concentration of the measuring object.

Similarly, the reduction reaction of oxygen occurring on the cathode as expressed by the formula (1) yields hydrogen peroxide as an intermediate product, which diffuses through the electrolytic solution to cause an extra oxidation reaction other than that expressed by the formula (2) when reaching the anode, preventing provision of an accurate output current corresponding to the oxygen concentration of the measuring object.

The above discussion was for the case of a two-pole type oxygen electrode in which a cathode and an anode compose a set of component electrodes. The same discussion is also substantially applicable to a three-pole type oxygen electrode when assuming a cathode substituted by a working electrode and an anode substituted by counter and reference electrodes.

As described above, the miniaturized oxygen electrode has a problem in that an increased electrolyte concentration for ensuring the electrolyte amount necessary for operation causes formation of a complex of the electrolyte components on the anode or its equivalents, which are undesirablly reduced on the component electrode on which reduction of oxygen alone should occur i.e., the cathode or its equivalents, and on the other hand, an intermediate product such as $OH^-$ formed on this electrode causes an extra oxidation reaction on the other component electrodes (the anode or its equivalents), with the result that an accurate output current cannot be maintained during a long period of operation.

SUMMARY OF THE INVENTION

The object of the present invention is to provide a miniaturized oxygen electrode which can be mass-produced at a high efficiency by collectively and uniformly processing a substrate as a whole, a production process thereof, and an electrolyte composition able to be advantageously used therefor.

To achieve the above object according to the first aspect of the present invention, there is provided an electrolyte composition for screen printing, comprising:
an organic solvent;
an inorganic salt in the form of a fine powder able to pass through a screen printing mesh, the salt powder being dispersed in the organic solvent; and
polyvinyl pyrrolidone dissolved in the organic solvent.

The electrolyte composition is screen-printed to form an electrolyte-containing material on a substrate.

The inorganic salt is preferably selected from potassium chloride and sodium chloride.

The inorganic salt used as an electrolyte must be in the form of a fine powder which can pass through the screen printing mesh, for example, in the form of a fine particle having a diameter not larger than 50 $\mu m$.

The organic solvent used in the present invention is preferably an alcohol such as butanol, pentanol, or hexanol.

The present inventive electrolyte composition is prepared by dispersing an inorganic salt such as potassium chloride, which is a superior electrolyte, in the form of a fine particle adapted for screen printing, in a high molecule polymer dissolved in an organic solvent. The present invention uses polyvinyl pyrrolidone as the high molecule polymer. An inorganic salt such as potassium chloride in the form of a fine particle may be prepared either by pulverizing a solid material or by pouring an aqueous solution containing an inorganic salt in saturation or in a high concentration near saturation into an organic solvent such as alcohol and acetone, which can be mixed with water in any proportion, to precipitate fine particles. Either method provides a powder of fine particles having a uniform size.

The present inventive electrolyte composition may further comprise a buffering agent, to ensure a constant pH (hydrogen ion concentration) of the electrolyte. The buffering agent is a salt exhibiting a buffering effect, such as phosphate, acetate, borate, citrate, phthalate, tetraborate, glycine salt, and tris(hydroxymethyl- )aminomethane salt, and is used in the form of a fine powder like the potassium chloride powder.

According to the second aspect of the present invention, there is also provided a miniaturized oxygen electrode comprising:
- an electrically insulating substrate;
- an electrolyte-containing material disposed on the substrate;
- a set of component electrodes in contact with the electrolyte-containing material and disposed on the substrate; and
- an oxygen gas-permeable membrane covering the electrolyte-containing material;
- the electrolyte-containing material being formed by screen-printing on the substrate the electrolyte composition according to the first aspect of the present invention.

According to the third aspect of the present invention, there is provided a process of producing a miniaturized oxygen electrode, comprising the steps of:
- preparing an electrically insulating substrate;
- forming an electrolyte-containing material on the substrate; and
- forming on the substrate a set of component electrodes in contact with the electrolyte-containing material;
- forming an oxygen gas-permeable membrane covering the electrolyte-containing material;
- the forming of the electrolyte-containing material being carried out by screen-printing on the substrate the electrolyte composition according to the first aspect of the present invention.

According to the second and third aspects of the present invention, a fine powder of an inorganic salt, polyvinyl pyrrolidone, and an organic solvent are blended to form an electrolyte composition in the form of a paste, which is then applied to a substrate at predetermined portions collectively by screen printing. The printed electrolyte composition, when dried, forms a dense film such that an oxygen gas-permeable membrane can be properly formed thereon.

According to the fourth aspect of the present invention, there is provided a miniaturized oxygen electrode comprising:
- an electrically insulating substrate;
- an electrolyte-containing material disposed on the substrate;
- a set of component electrodes disposed on the substrate, each having an end in contact with the electrolyte-containing material and an end for external electrical connection; and
- an oxygen gas-permeable membrane covering the substrate in a portion containing the electrolyte-containing material;
- the oxygen gas-permeable membrane being removed from the substrate in a region containing the end for external electrical connection, by removing a removable cover film interposed between the substrate and the oxygen gas-permeable membrane.

According to the fifth aspect of the present invention, there is provided a process for producing a miniaturized oxygen electrode, comprising the steps of:
- preparing an electrically insulating substrate;
- forming an electrolyte-containing material on the substrate;
- forming on the substrate a set of component electrodes each having an end in contact with the electrolyte-containing material and an end for external electrical connection; and
- forming a removable cover film on the substrate in a region to be exposed in the following removing step, the region containing the component electrode end for external electrical connection;
- forming an oxygen gas-permeable membrane covering the substrate surface including the region of the removable cover film; and
- removing the oxygen gas-permeable membrane by peeling the removable cover film away from the substrate surface, to expose the to-be-exposed region of the substrate and thereby shape the oxygen gas-permeable membrane to a predetermined pattern.

The process according to the fifth aspect of the present invention preferably comprises the steps of:
- screen-printing a thermosetting resin onto the to-be-exposed region of the substrate;
- heating the resin to cure the resin to form a resin film as the removable cover film;
- forming the oxygen gas-permeable membrane covering the substrate surface including the region of the resin film;
- peeling the resin film to expose the to-be-exposed region, and thereby shape the oxygen gas-permeable membrane to a predetermined pattern.

According to the fourth and the fifth aspects of the present invention, an oxygen gas-permeable membrane is formed selectively or patterned to cover the necessary region of the substrate surface by first covering a region of substrate to be exposed with a removable cover film, applying a resin for forming an oxygen gas-permeable membrane onto the whole surface of the substrate by spin coating, and then peeling or exfoliating the removable cover film to thereby remove the oxygen gas-permeable membrane together with the cover film in the region of substrate to be exposed. The present invention uses, as the material of the removable cover film, a thermosetting resin, a solution of polyvinylchloride in an organic solvent, or other resins. Such resins are applied to the predetermined region of a substrate by screen printing, and then cured by heating or drying to form a removable cover film.

The electrically insulating substrate, on which the present inventive miniaturized oxygen electrode is formed, may be an electrically insulating substrate having a flatness and a smoothness sufficient for forming a miniaturized oxygen electrode by using the semiconductor process. A silicon wafer is most advantageously used as the insulating substrate, from the viewpoint of the application of the production process of silicon semiconductors currently most generally used.

The present invention may be directly applied to miniaturized oxygen electrodes formed on insulating substrates other than the silicon wafer. Namely, a miniaturized oxygen electrode is produced by using a flat substrate of an electrically insulating substance such as glass, quartz and plastics, in such a manner that a component electrode pattern is formed on the substrate, an electrolyte-containing material is filled in the oxygen sensing site by screen printing an electrolyte composition of the present invention, and then an oxygen gas-permeable membrane is selectively formed or patterned by the steps including forming a removable cover film by screen-printing a thermosetting resin, etc., on the pad portion, i.e., the region of the substrate including the component electrode end for external electrical connection. It will be easily understood that, even in this case, the present invention also provides an advantage in that a number of miniaturized oxygen electrodes are formed collectively at one time on the whole region of an integral substrate.

According to the present invention, the screenprinted electrolyte composition contains a fine powder of an inorganic salt or an electrolyte not dissolved but dispersed in an organic solvent, and therefore, the inorganic salt, even when dried, does not form a brittle crystal but remains a fine powder, and this enables an electrolyte-containing material in the form of a dense solid material to be formed. The thus obtained electrolyte-containing material is essentially composed of the inorganic salt and polyvinyl pyrrolidone. Upon operating a miniaturized oxygen electrode, water is introduced into the electrolyte-containing material. Both the inorganic salt and polyvinyl pyrrolidone are water-soluble and completely dissolved in the introduced water, and thus the present inventive electrolyte-containing material satisfies the requirement for a miniaturized oxygen electrode that it remains in a solid state during the formation of an oxygen gas-permeable membrane and forms an aqueous solution when the miniaturized oxygen electrode is operated.

Potassium chloride and sodium chloride are superior electrolytes and can be advantageously used as the inorganic salt according to the present invention, to obtain the best performance of a miniaturized oxygen electrode.

The addition of a salt having a pH buffering effect, such as phosphate, to the present inventive electrolyte composition ensures that the electrolyte has a constant pH. As the electrochemical reaction in the oxygen electrode depends on the pH value, the constant pH improves the stability of the oxygen electrode performance.

The miniaturized oxygen electrode according to the present invention is produced by filling an electrolyte composition containing an inorganic salt as an electrolyte in the form of a fine powder, collectively in all of the predetermined portions of a substrate, by screen printing, to thereby ensure a uniform filling operation and a high productivity.

The process of producing a miniaturized oxygen electrode according to the present invention fills an electrolyte composition containing an inorganic salt as an electrolyte in the form of a fine powder, collectively in all of the predetermined portions of a substrate by screen printing, and thereby ensures a uniform filling operation and mass-production of a miniaturized oxygen electrode even when the filled portion has a complicated shape. The present inventive production process can also advantageously cope with any increase in the number of filling portions associated with an enlargement of the substrate size.

The miniaturized oxygen electrode according to the present invention ensures a high productivity even when the oxygen gas-permeable membrane and the exposed portion have a complicated shape, because the oxygen gas-permeable membrane is patterned (or selectively formed) by removing a cover film formed in a predetermined shape. The oxygen gas-permeable membrane is applied collectively on the entire substrate surface by spin-coating, and thereby a high productivity is ensured and an oxygen gas-permeable membrane having a uniform thickness over the entire substrate surface is formed.

The miniaturized oxygen electrode according to the present invention can be produced at a high productivity by effectively forming an oxygen gas-permeable membrane having a uniform thickness over the entire substrate surface, i.e., by first covering a substrate region to be exposed with a removable cover film, forming an oxygen gas-permeable membrane collectively on the entire substrate surface, and then peeling or exfoliating the removable cover film to selectively form or pattern the oxygen gas-permeable membrane.

The process according to the present invention can easily cope with a complicated pattern of oxygen gas-permeable membrane and with any increase in the number of portions to be exposed, because an oxygen gas-permeable membrane is patterned through the steps of: applying a thermosetting resin of a resin dissolved in an organic solvent to the to-be-exposed portions by screen printing; curing the applied resin by heating or drying to form a removable cover film; and then peeling or exfoliating the removable cover film.

A further object of the present invention is to provide a miniaturized oxygen electrode in which a stable operation over a long period of time is ensured by preventing the reduction reaction of chemical species other than oxygen on a component electrode (the cathode or its equivalents) on which reduction reaction of oxygen alone should occur and also preventing undesirable extra oxidation reactions on the other component electrodes (the anode or its equivalents) caused by an intermediate product (such as $OH^-$) formed on the former component electrode (cathode or its equivalents).

To achieve the above object according to the present invention, there is provided a miniaturized oxygen electrode which comprises:

an electrically insulating substrate;
an electrolyte-containing material disposed on the substrate and capable of serving as an electrolytic solution when supplied with water;
a set of component electrodes disposed on the substrate and composed of a first component electrode on which a reduction reaction of oxygen dissolved in the electrolytic solution occurs when the miniaturized oxygen electrode is operated and one or more second component electrodes other than the first component electrode, the first component electrode being interconnected with the second component electrodes through the electrolyte-containing material;
an oxygen gas-permeable membrane covering the electrolyte-containing material; and
the electrolyte-containing material having a length for providing a sufficient distance along the interconnection between the first and second component electrodes such that any electroactive substances, formed on one of the first and second component electrodes during the operation of the miniaturized oxygen electrode, are prevented from reaching the other of the first and second component electrodes when diffusing along the length of the electrolytic solution.

According to the present invention, an electrolyte-containing material has a sufficiently long interconnection between first and second component electrodes such that any electroactive substances, formed on the second component electrodes during an operation of the oxygen electrode, are prevented from reaching the first component electrode when diffusing through the electrolytic solution, thereby avoiding the occurrence of reduction reactions of chemical species other than oxygen on the first component electrode on which reduction reaction of oxygen alone should occur while, to the contrary, electroactive substances such as OH⁻ formed on the first component electrode are prevented from reaching the second component electrodes, thereby avoiding the occurrence of undesired extra oxidation reactions on the second component electrodes, so that an accurate output current is stably maintained during a long period of operation.

When a miniaturized oxygen electrode has a two-pole type structure, the set of component electrodes is composed of a cathode acting as the first component electrode and an anode acting as the second electrode.

When a miniaturized oxygen electrode has a three-pole type structure, the set of component electrodes is composed of a working electrode, a counter electrode and a reference electrode, the working electrode acting as the first component electrode and the others acting as the second component electrodes.

Preferably, the electrolyte-containing material is sufficiently slender or has a width sufficiently small so as to more effectively suppress diffusion of the electroactive substances from one of the first and second electrodes to the other over the length of the electrolyte-containing material.

The electrolyte-containing material preferably has a zigzag or meandering form to provide a sufficient length of an electrolytic solution in a minimum chip size and thereby favor the miniaturization of oxygen electrodes.

The present invention is advantageously applicable to both two- and three-pole type structures of oxygen electrodes.

A miniaturized oxygen electrode of the present invention is advantageously produced by a process in which the electrolyte-containing material is formed by printing a composition containing the electrolyte onto the electrically insulating substance.

BRIEF DESCRIPTION OF THE DRAWINGS

FIG. 1 shows the essential arrangement of a conventional oxygen electrode, in sectional view;

FIGS. 13A and 13B show a plan view of a two-pole type miniaturized oxygen electrode formed on a silicon wafer according to the present invention, in a complete form and a form in which a gas-permeable membrane is omitted for depicting the inside arrangement, respectively;

FIGS. 14A through 14I show a process sequence for producing a two-pole type miniaturized oxygen electrode on a silicon wafer according to the present invention, in (a) a plan view and (b) a sectional view along the line I—I of (a);

FIGS. 15A and 15B show an arrangement of a three-pole type miniaturized oxygen electrode formed on a silicon wafer according to the present invention, in a complete form and a form in which a gas-permeable membrane is omitted for depicting the inside arrangement, respectively;

FIGS. 17A through 17E show a process sequence for producing a two-pole type miniaturized oxygen electrode on a glass plate according to the present invention in (a) a plan view and (b) a sectional view along the line I—I of (a)

DESCRIPTION OF THE PREFERRED EMBODIMENTS

Example 1

Figure 2A:
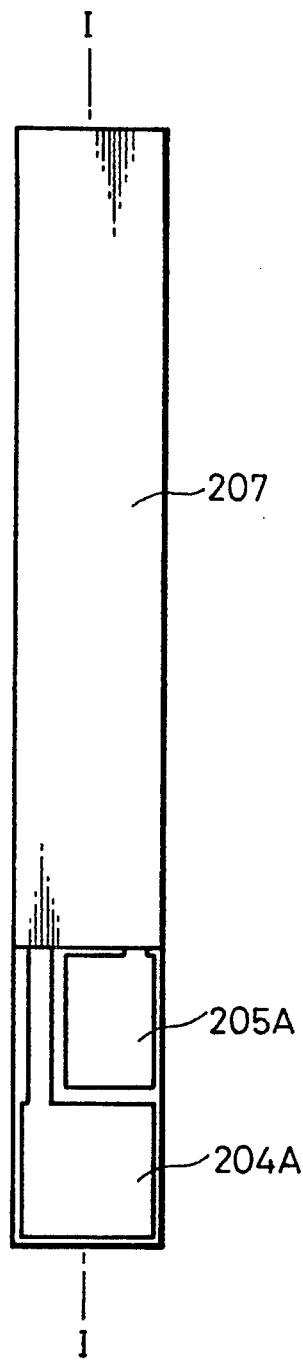
FIGS. 2(a) through (c) show a miniaturized oxygen electrode in plan view (a, b) and sectional view (c)
Figure 2B:
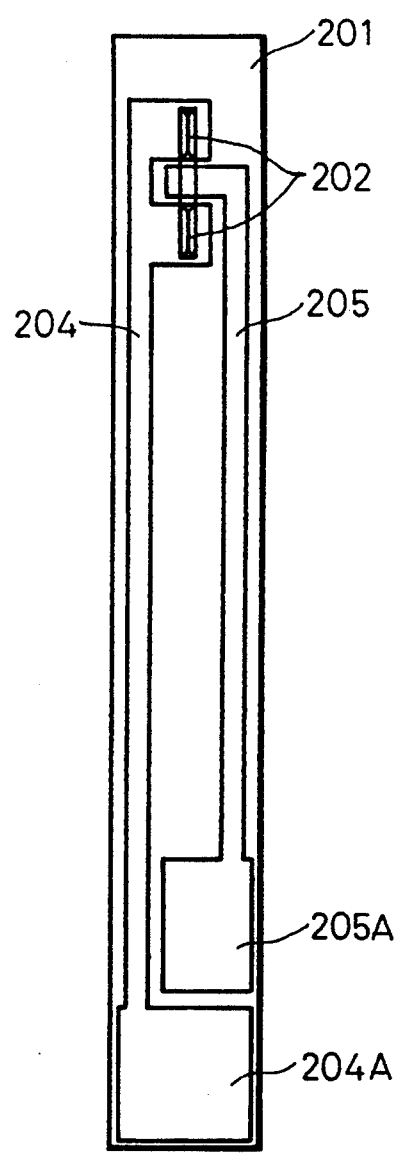
Figure 2C:
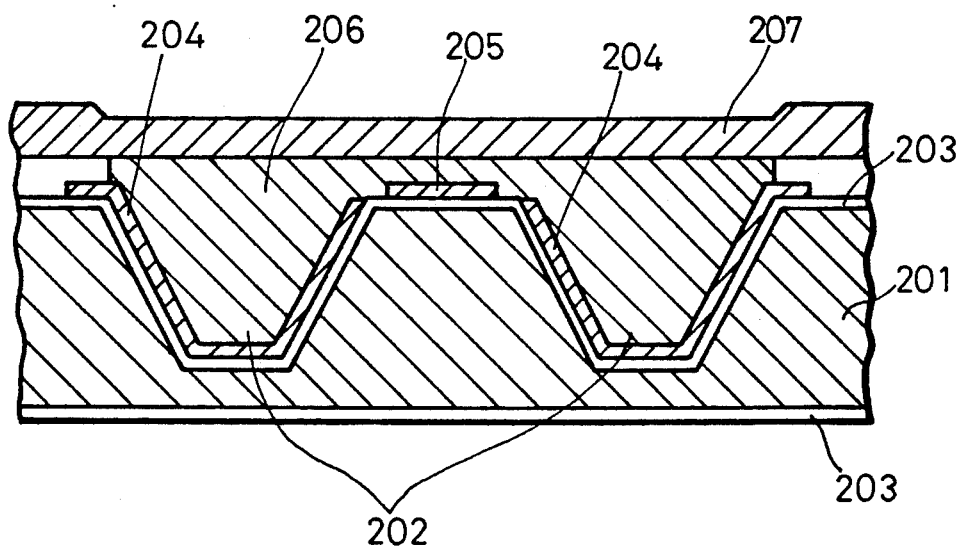
Figure 3A:
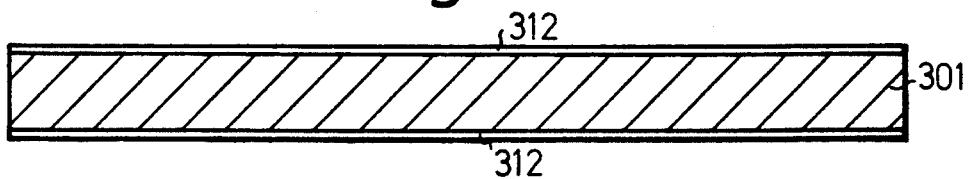
FIGS. 3(a) through (n) show a process sequence according to the present invention, in sectional and plan views.
Figure 3B:
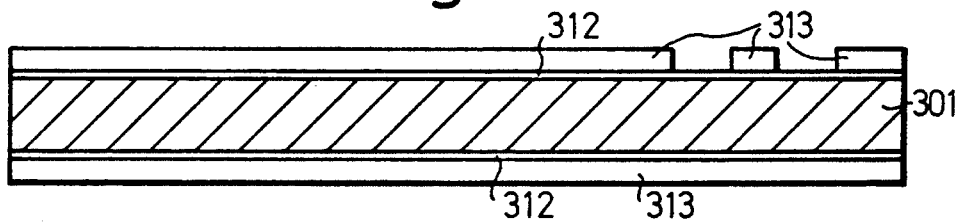
Figure 3C:
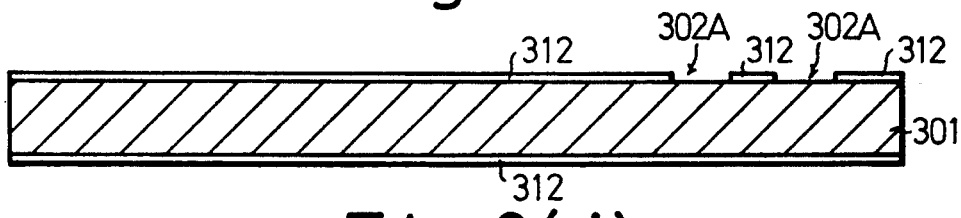
Figure 3D:
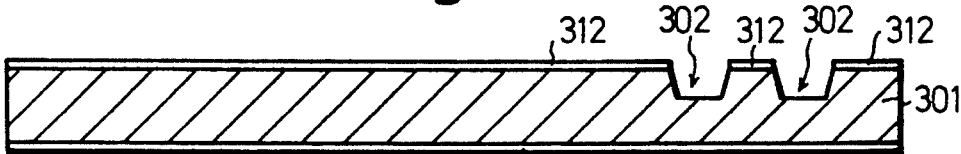
Figure 3E:
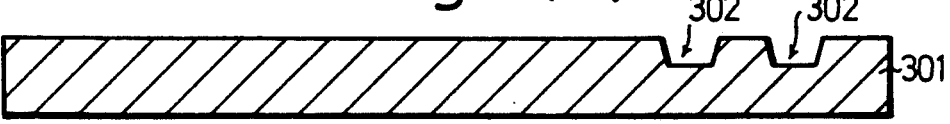
Figure 3F:
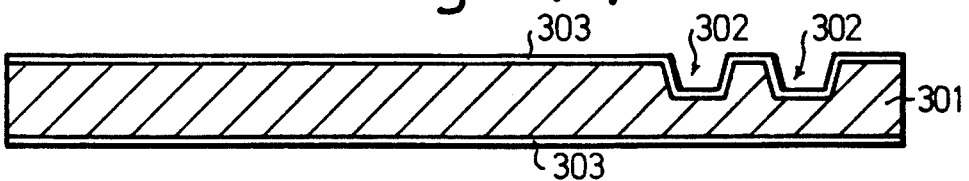
Figure 3:
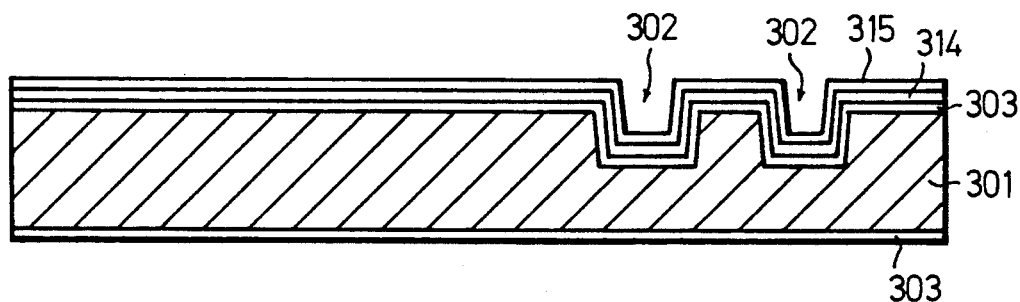
Figure 3:
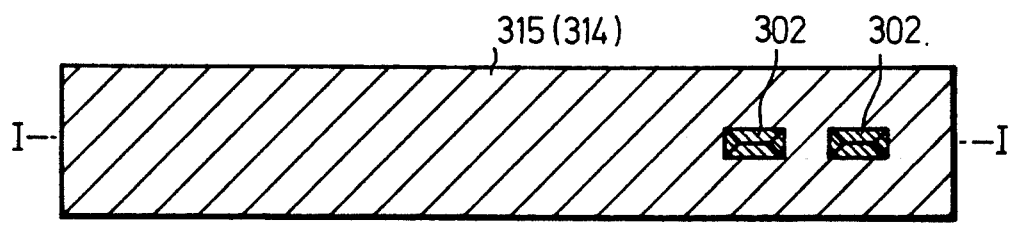
Figure 3:
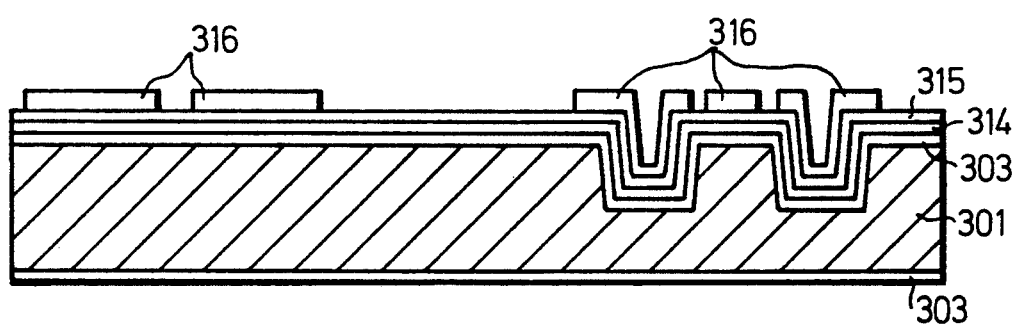
Figure 3:
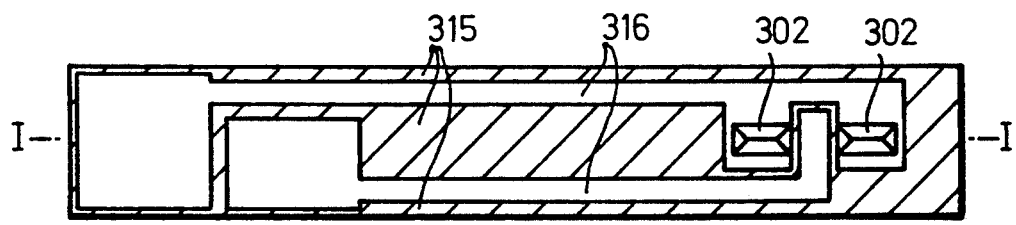
Figure 3:
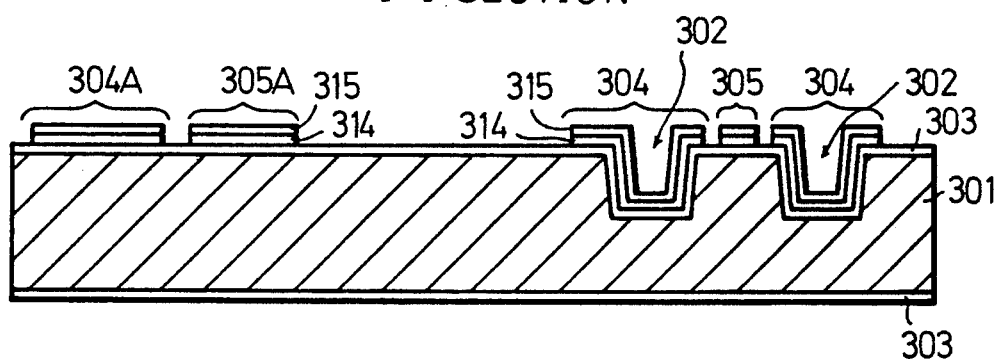
Figure 3:
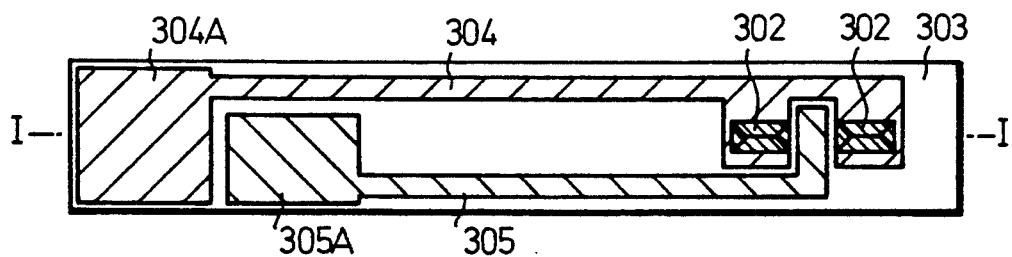
Figure 3:
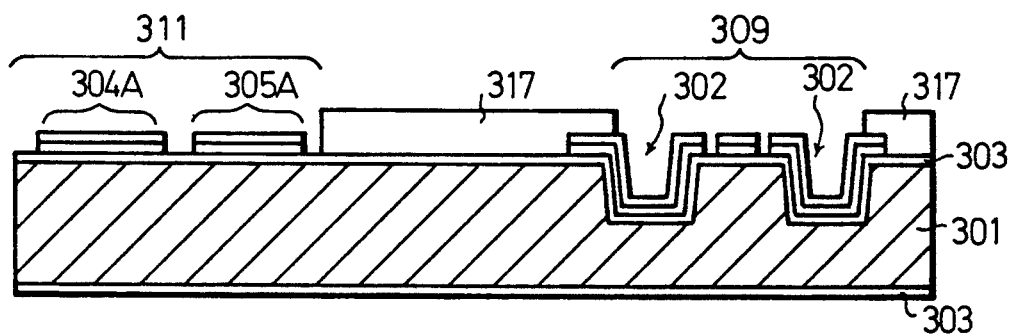
Figure 3:
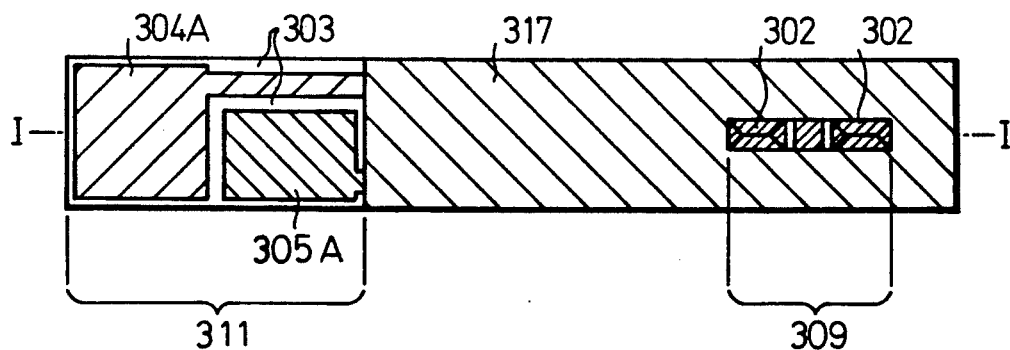
Figure 3:
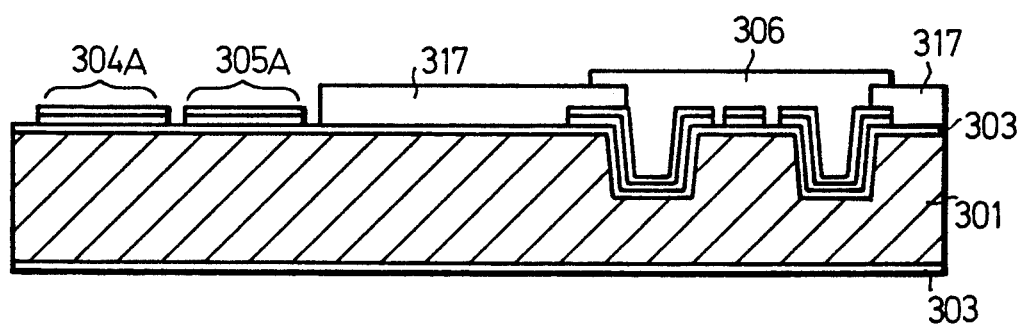
Figure 3:
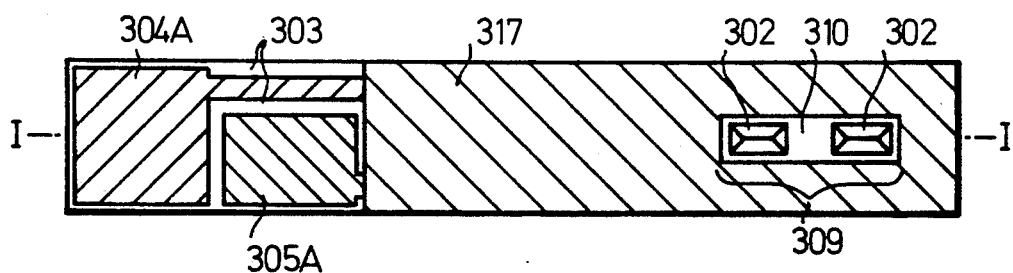
Figure 3:
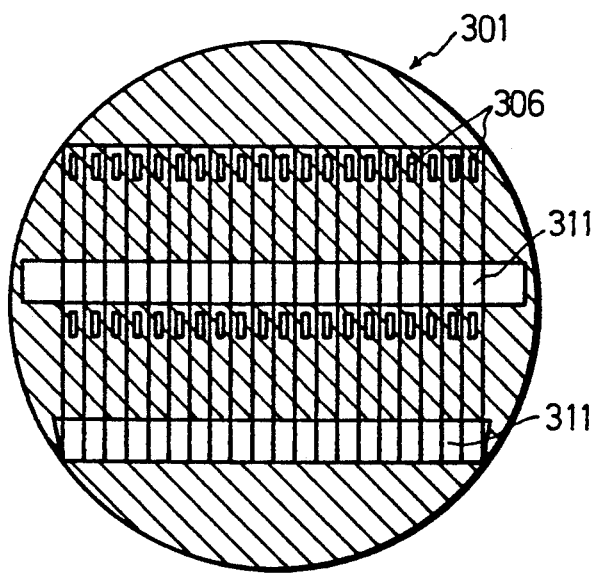
Figure 3:
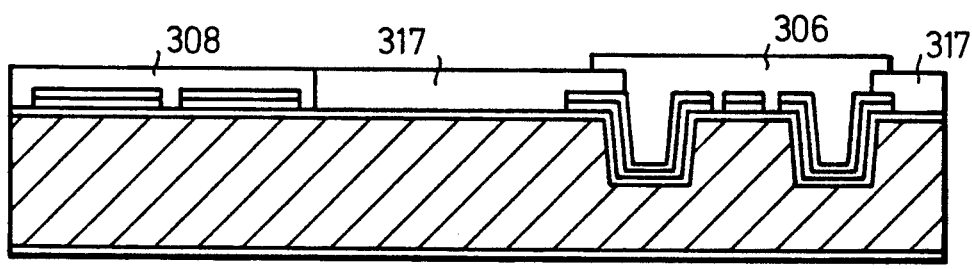
Figure 3:
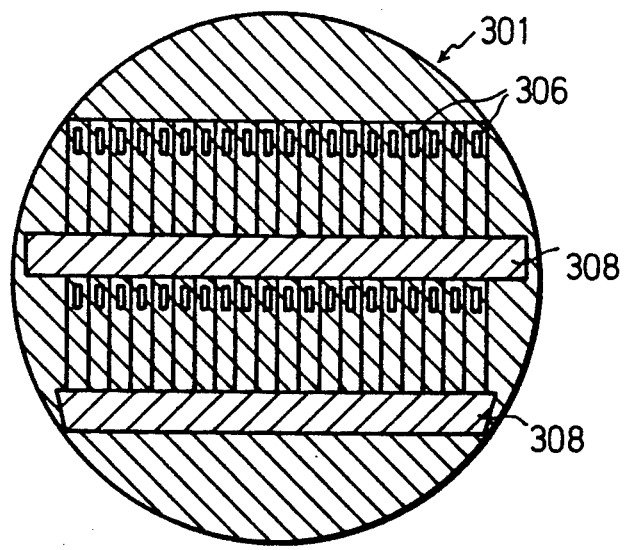
Figure 3:
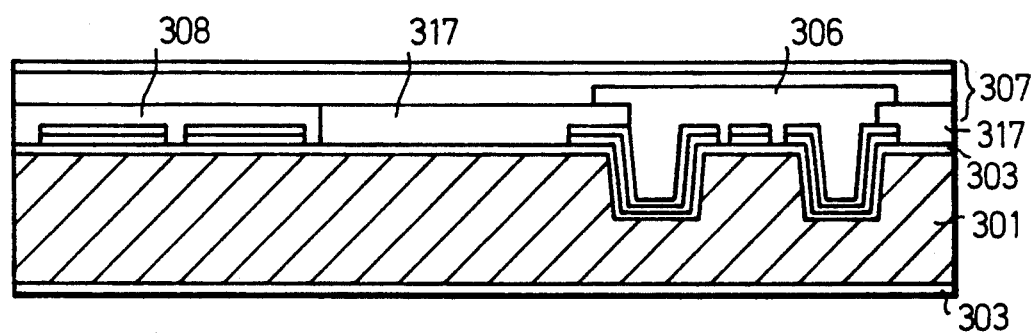
Figure 3:
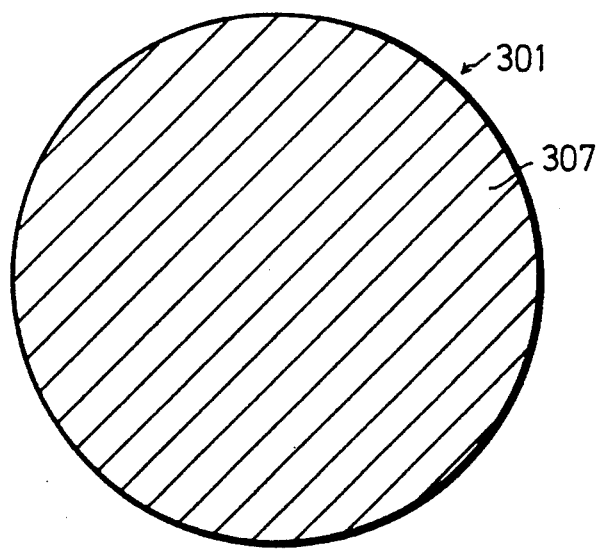
Figure 3:
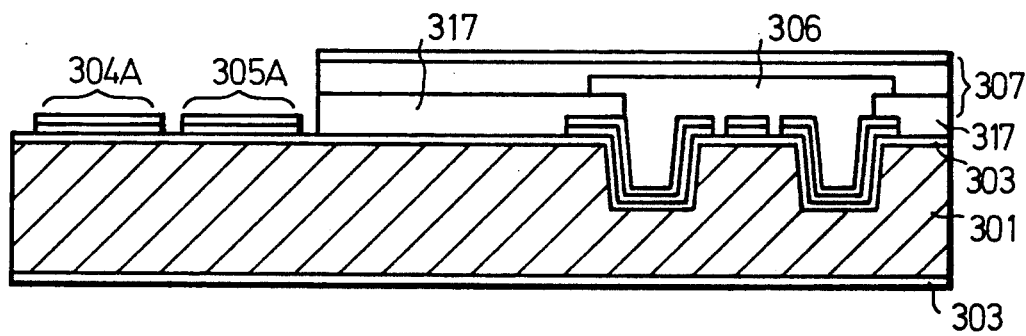
Figure 3:
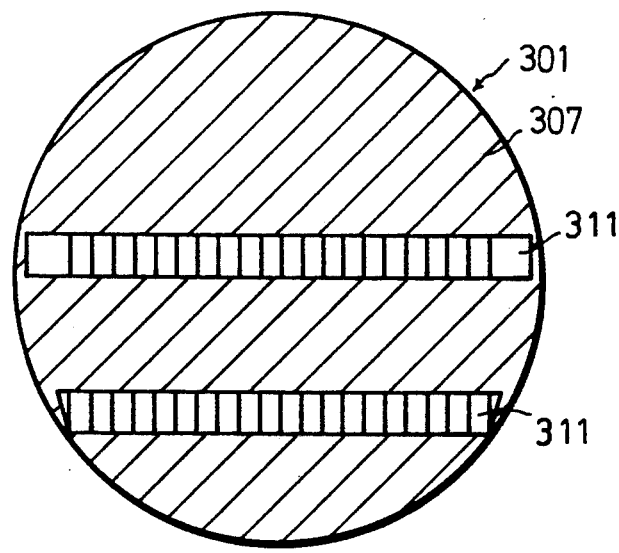

Referring to FIG. 3, a process sequence for producing a miniaturized oxygen electrode according to the present invention by using a silicon wafer will be described below. Although the sequence is described for the case in which a miniaturized oxygen electrode is formed on a 2-inch silicon wafer, for simplicity, essentially the same process sequence can be also used for a larger wafer. The Figures depict the wafer in which the corresponding process step is completed.

Step 1: Cleaning Wafer

A 2-inch silicon wafer 301 (400 μm thick, (100) plane) was thoroughly cleaned with a mixed solution of hydrogen peroxide and ammonia and with a concentrated nitric acid.

Step 2: Forming $SiO_2$ Layer (FIG. 3(a))

The wafer 301 was wet-thermally oxidized at 1000° C. for 200 min. to form a 0.8 μm thick $SiO_2$ layer 312 on both sides of the wafer. The $SiO_2$ layer 312 is to be patterned in the following step 4 and used as a mask when anisotropically etching the silicon wafer in the following step 5.

Step 3: Forming Resist Pattern (FIG. 3(b))

A negative-type photoresist (Tokyo Ohka Kogyo Co., Ltd., OMR-83, viscosity 60 cP) was applied on the entire upper surface of the wafer, prebaked at 80° C. for 30 min. and was subjected to a photolithography treatment to form a resist pattern 313. The resist pattern 313 covers the upper surface of the wafer 301 except for a region 302A at which grooves 302 (FIG. 3(d)) for receiving an electrolyte-containing material are to be formed in the following step 5. The resist pattern 313 serves as a mask upon etching the $SiO_2$ layer 312 in the following step 4. The same photoresist was applied on the lower surface of the wafer 301, which was then baked at 150° C. for 30 min.

Step 4: Etching $SiO_2$ Layer (FIG. 3(c))

The wafer 301 was immersed in en etchant for $SiO_2$ (50%HF/1ml+$NH_4F$/6 ml) to partially remove the $SiO_2$ layer 312 in the portion 302A not covered with the photoresist 313. The wafer 301 was then immersed in a mixed solution of connected sulfuric acid and hydrogen peroxide, to remove the photoresist 313.

Step 5: Anisotropically Etching Silicon Wafer (FIG. 3(d))

The wafer 301 was immersed in an etchant for silicon (35% KOH) at 80° C. to anisotropically etch the silicon wafer 301 by using the $SiO_2$ layer as a mask, and thereby forming two 300 μm deep grooves 302 for receiving an electrolyte-containing material. After the anisotropic etching was finished, the wafer 301 was cleaned with pure water.

Step 6: Removing $SiO_2$ Layer (FIG. 3(e))

Subsequent to the water cleaning, the $SiO_2$ layer 312 was removed by the same operation as that performed in Step 4.

Step 7: Forming $SiO_2$ Layer (FIG. 3(f))

The same operations as performed in Steps 1 and 2 were carried out to effect a thermal oxidation of the wafer 301, and thereby form a 0.8 μm thick $SiO_2$ layer 303 on the entirety of both sides of the wafer 301. The thus-formed $SiO_2$ layer 303 functions as an insulating layer of a miniaturized oxygen electrode or the final product.

Step 8: Forming Thin Layers of Chromium and Silver (FIGS. 3(g1), 3(g2))

A 400 Å thick chromium thin layer 314 and a 4000 Å thick silver thin layer 315 overlying on the chromium layer 314, were formed on the entire upper surface of the wafer 301 by vacuum deposition. The silver thin layer 315 is an electroconductive layer composing the substantial portion of component electrodes (anode and cathode) and the chromium thin layer 314 is a ground layer for ensuring an adhesion of the silver thin layer 315 to the $SiO_2$ insulating layer 303 formed on the wafer 301.

Step 9: Forming Photoresist Pattern (FIGS. 3(h1), 3(h2))

This step provides a photoresist pattern 316 to be used as a mask in the following Steps 10 and 11, in which the silver thin layer 315 and the chromium thin layer 314 are etched to thereby effect a patterning of component electrodes (anode and cathode) of a miniaturized oxygen electrode.

A positive-type photoresist (Tokyo Ohka Kogyo Co., Ltd., OFPR-800, viscosity 20 cP or OFPR-5000, viscosity 50 cP) was dropped on the wafer 301 to uniformly cover the wafer 301. The photoresist is preferably dropped in an amount such that it spreads just to the wafer circumferential edge. The wafer 301 was prebaked at 80° C. for 30 min.

The wafer 301 was pattern-aligned with a glass mask by a mask aligner, exposed to light, and developed to form a photoresist pattern 316. The exposure and development cycle was repeated to ensure a complete exposure of the positive-type photoresist layer, which is too thick to complete the exposure over the thickness at one time.

Step 10: Etching Thin Layers of Silver and Chromium (FIGS. 3(i1) and 3(i2))

The wafer 301 was immersed in an etchant for silver ($NH_3$ water/1 ml+$H_2O_2$/1 ml+water/20 ml) to remove a bare portion of the silver layer, and thereby form the substantial portion of component electrodes.

The wafer was then immersed in an etchant for chromium (NaOH/0.5 g+$K_3Fe(CN)_6$/1 g+water/4 ml) to remove a bare portion of the chromium layer 314.

Step 11: Forming Photoresist Pattern (FIGS. 3(j1) and 3(j2))

This step provides a photoresist pattern 317 for defining the oxygen sensing site of a miniaturized oxygen electrode.

A layer 317 of a negative-type photoresist (Tokyo Ohka Kogyo Co., Ltd., OMR-83, viscosity 60 cP) was formed on the wafer 301 to cover the wafer surface in the portion other than a region 309 of the oxygen sensing site (two grooves and a flat plateau therebetween) and a pad region 311, at which the pad portions 304A and 305A of component electrodes 304 and 305 are to be formed. This is performed by applying the photoresist to the wafer surface, prebaking the wafer at 80° C. for 30 min, and exposing to light and developing the photoresist layer. Thereafter, the photoresist layer was postbaked at 150° C. for 30 min.

Step 12: Screen-Printing Electrolyte Composition FIGS. 3(k1), 3(k2) and 3(k3))

An electrolyte composition was screen-printed at the oxygen sensing site 309 (two grooves and a flat plateau therebetween) defined by the photoresist 317, to form an electrolyte-containing material 306. The preparation of the electrolyte used will be described later.

Step 13: Forming Pad Region Cover Film (FIGS. 3(l1) and 3(l2))

A thermosetting release coating (Fujikura Kasei Co. XB-801) was screen-printed at the pad region 311 at a thickness of 100 μm and cured by heating at 150° C. for 10 min. to form a removable cover film 308.

Step 14: Forming Oxygen Gas-Permeable Membrane FIGS. 3(m1) and 3(m2))

An oxygen gas-permeable membrane 307 having a double-layered structure was formed on the wafer 301 to entirely cover the upper surface of the wafer 301. The lower layer of the membrane 307 was first formed by applying a negative-type photoresist (Tokyo Ohka Kogyo Co., Ltd., OMR-83, viscosity 100 cP) to the wafer 301 by spin coating, prebaking at 80° C. for 30 min., exposing the entire wafer surface to light and developing, and postbaking at 150° C. for 30 min. The upper layer of the membrane 307 was then formed by applying a silicone resin (Toray-Dow Corning Silicone Co. SE9176) to the wafer 301 by spin coating and curing the coated resin by heating at 70° C. for 30 min. in an oven moistened by water contained in a Petri dish or a beaker placed in the oven.

Step 15: Exposing Pads (FIGS. 3(n1) and 3(n2)

The cover film 308 formed on the pad region 311 was peeled with a pincette to selectively remove the oxygen gas-permeable membrane in that region, and thereby expose the pads 304A and 305A of a miniaturized oxygen electrode.

Step 16: Separating Miniaturized Oxygen Electrodes

A number of miniaturized oxygen electrodes were collectively formed on the wafer 301 at one time by the preceding Steps 1 through 15 and were cut into chips by a dicing saw. The shown example provides forty chips of miniaturized oxygen electrodes at one time.

Example 2

Miniaturized oxygen electrodes were produced by the same process sequence as that of Example 1, except that Step 13 of forming a pad region cover film was modified as follows:

Step 13': Forming Pad Region Cover Film (Modified)

Polyvinylchloride resin dissolved in tetrahydrofuran was screen-printed at the pad region 311 at a thickness of 50 μm and cured by heating at 70° C. to form a cover film 308.

The electrolyte composition according to the present invention used in Step 12 of Examples 1 and 2 was prepared in the following manner.

PREPARATION PROCEDURE 1: PROVIDING FINE POWDER OF INORGANIC SALT

Fine particles of potassium chloride or sodium chloride were formed by either of the following procedures (a) and (b):

(a) A solid material of potassium chloride or sodium chloride was pulverized to fine particles having a diameter of 10 μm or less by a pulverizer (Fritsch Co. Type P-5).

(b) A saturated aqueous solution of potassium chloride or sodium chloride was prepared. The solution was poured into an organic solvent such as ethanol, propanol, or acetone of an amount of ten times the solution, through a Teflon* ball filter (Iuchiseieido Co., pore diameter 10 μm). The organic solvent was thoroughly agitated by a stirrer during the pouring. This provided a precipitation of fine particles of inorganic salt, which was collected by a glas filter, washed two or three times with a fresh organic solvent of the same kind, and dried to obtain fine particles having a diameter of 10 μm or less.

(*) "Teflon": trademark of Du Pont Co. for polytetrafluoroethylene (PTFE)

PREPARATION PROCEDURE 2: BLENDING ELECTROLYTE COMPOSITION

The above-obtained fine particles of inorganic salt, polyvinyl pyrrolidone, and an organic solvent were blended to form an electrolyte composition in the form of a paste. The following is an example of the thus-blended composition.

| Electrolyte Composition: Case 1 | |
| --- | --- |
| Potassium chloride fine particle | 0.25 g |
| Polyvinyl pyrrolidone | 1 g |
| Pentanol | 5 g |

The blending may be carried out in a manner such that the electrolyte composition contains 30 to 70% of a solid part and the remainder of an organic solvent, the solid part containing 50 to 90% of an inorganic salt. The following is an example of the thus-blended composition.

| Electrolyte Composition: Case 2 | |
| --- | --- |
| Potassium chloride fine particle | 4 g |
| Polyvinyl pyrrolidone | 1 g |
| Pentanol | 5 g |

According to preferred embodiment of the present invention, an electrolyte composition further comprises a salt having a pH-buffering effect. Although a phosphate was added in the following case, the buffering agent used in the present invention may be selected from the group consisting of phosphates, accetates, borates, citrates, phthalates, tetraborates, glycine salts, and tris(hydroxymethyl)aminomethane salts.

An electrolyte composition with an addition of a phosphate as a buffering agent may be prepared in the following manner, for example.

PREPARATION PROCEDURE 1: PROVIDING FINE POWDER OF INORGANIC SALT

Fine particles of potassium chloride or sodium chloride were formed by either of the following procedures (a) and (b):

(a) 74.55 g of potassium chloride and 8.71 g of dipotassium hydrogen phosphate were weighed and pulverized to particles having a diameter of 10 μm or less by a pulverizer (Fritsch Co., Type P-5).

(b) 74.55 g of potassium chloride and 8.71 g of dipotassium hydrogen phosphate were weighed and dissolved in 230 ml of water. The aqueous solution was poured into an amount of ethanol ten times the amount of the solution, through a Teflon ball filter (Iuchiseieido Co., pore diameter 10 μm). The ethanol was thoroughly agitated by a stirrer during the pouring. This resulted in a precipitation of fine particles of inorganic salt, which was then collected by a glass filter, washed with a fresh ethanol two or three times, and dried to obtain fine particles having a diameter of 10 μm or less.

The fine particles of potassium chloride or sodium chloride and the fine particles of phosphate or a buffering agent may be separately prepared. For example, when a concentrated aqueous solution of potassium chloride or sodium chloride is formed, an aqueous solution of potassium dihydrogen phosphate and sodium dihydrogen phosphate (4:6 in molar ratio) can be separately formed. Both solutions are preferably in a saturation state, which provides a greater amount of fine particles, i.e., a high efficiency. Note that the weighed phosphates must be completely dissolved in water, because the proportion of the dissolved phosphates significantly affects the pH value. The thus-prepared aqueous solutions are poured into an organic solvent such as ethanol, in the same manner as described above, respectively, and the precipitated fine particles are collected.

PREPARATION PROCEDURE 2: BLENDING ELECTROLYTE COMPOSITION

The above-obtained fine particles of inorganic salts, polyvinyl pyrrolidone, and an organic solvent were blended to form an electrolyte composition in the form of a paste. The followings are examples of the thus-blended compositions.

| Electrolyte Composition: Case 3 | |
| --- | --- |
| Mixture of fine particles of potassium chloride and phosphate | 0.25 g |
| Polyvinyl pyrrolidone | 1 g |
| Pentanol | 5 g |
| Electrolyte Composition: Case 4 (fine particles of buffering agent separately formed) | |
| Potassium chloride fine particle | 3.5 g |
| Phosphate fine particle | 0.5 g |
| Polyvinyl pyrrolidone | 1 g |
| Pentanol | 5 g |

The performance of the miniaturized oxygen electrode produced in Examples 1 and 2 was tested by measuring the dissolved oxygen concentration of a 10 mM buffered phosphoric acid solution having a pH value of 7.0 at an applied voltage of 0.6 V and a temperature of 25° C.

Figure 4:
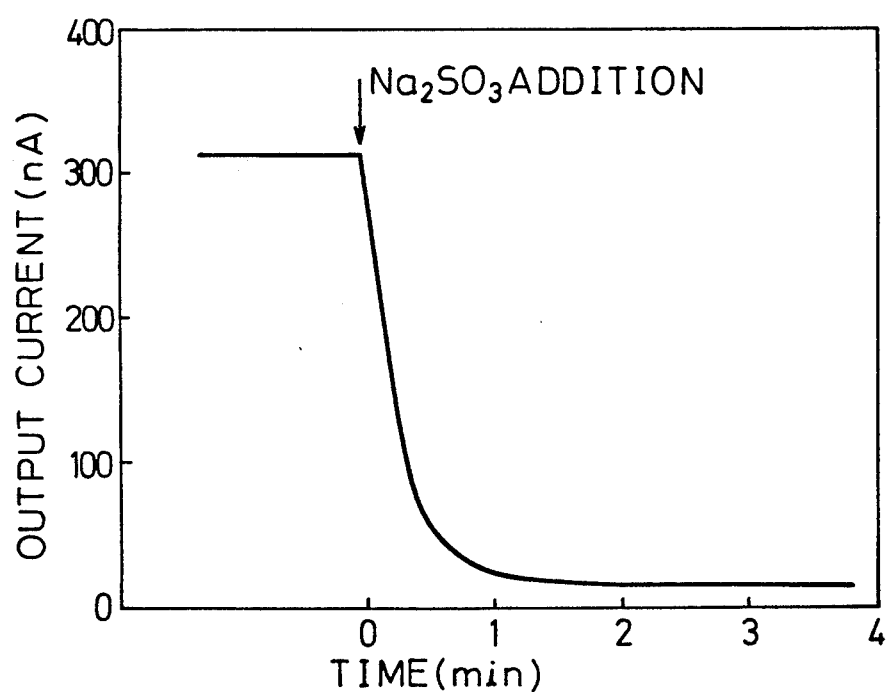
FIG. 4 is a graph showing a typical response of a miniaturized oxygen electrode according to the present invention, in terms of the relationship between the time elapsed from the addition of $Na_2SO_3$ and the output current.

FIG. 4 shows a response curve observed when sodium sulfite is added to a solution saturated with 100% oxygen, to instantaneously reduce the oxygen concentration to zero. The response time was 40 seconds, which corresponded to the variation of the dissolved oxygen concentration.

Figure 5:
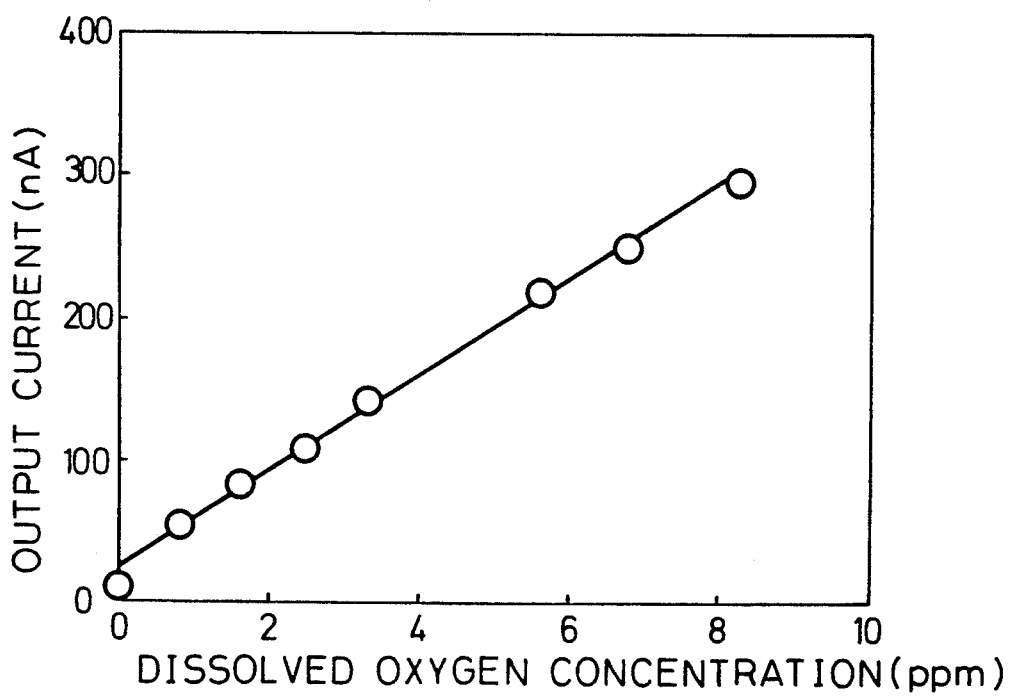
FIG. 5 is a graph showing the linear calibration curve of a miniaturized oxygen electrode according to the present invention, in terms of the relationship between the dissolved oxygen content and the output current.
Figure 6A:
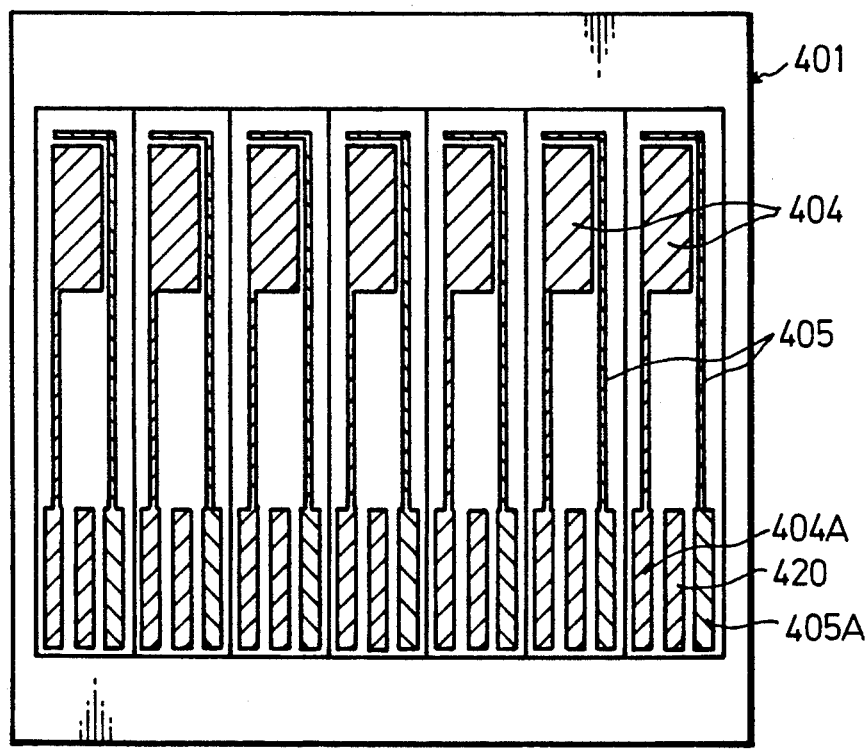
FIGS. 6(a) through (f) show a process sequence according to the present invention, in sectional and plan views.
Figure 6B:
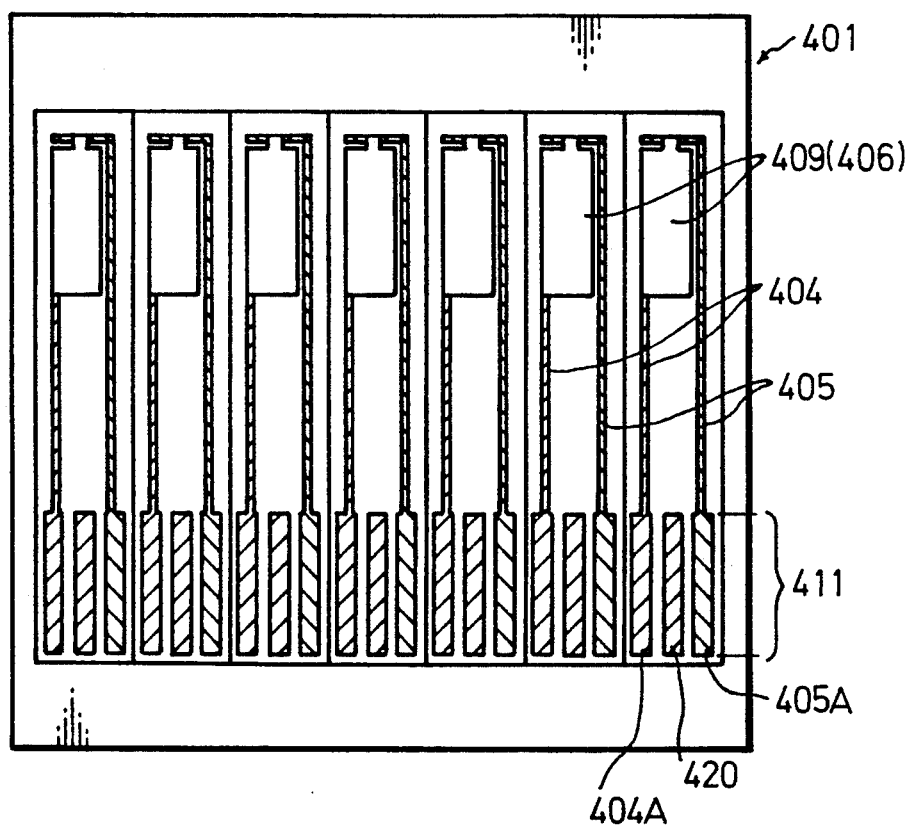
Figure 6C:
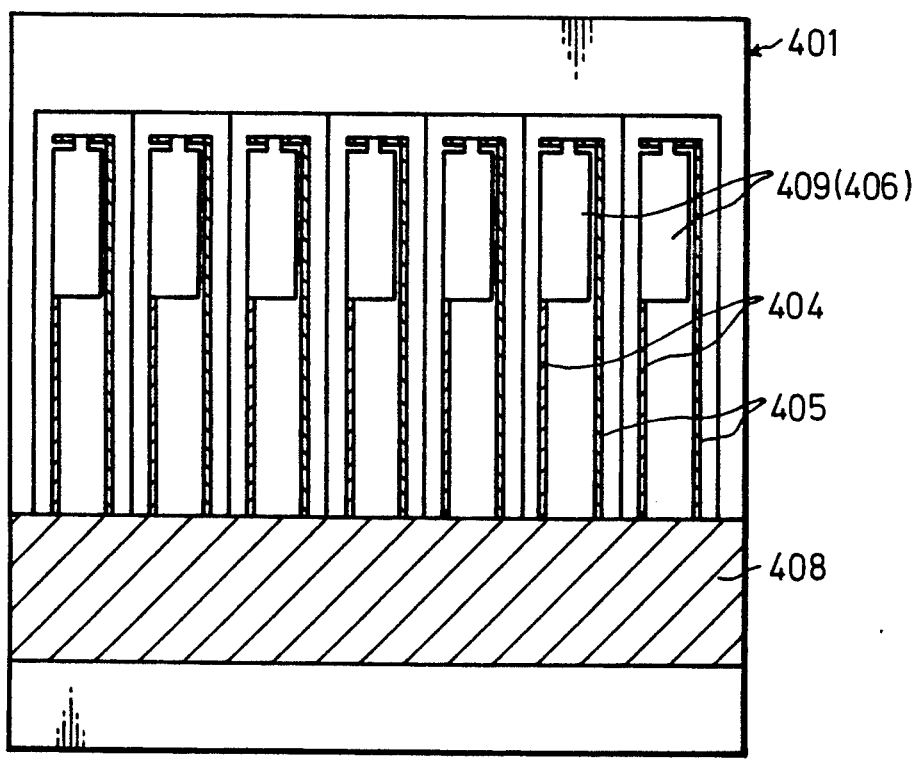
Figure 6D:
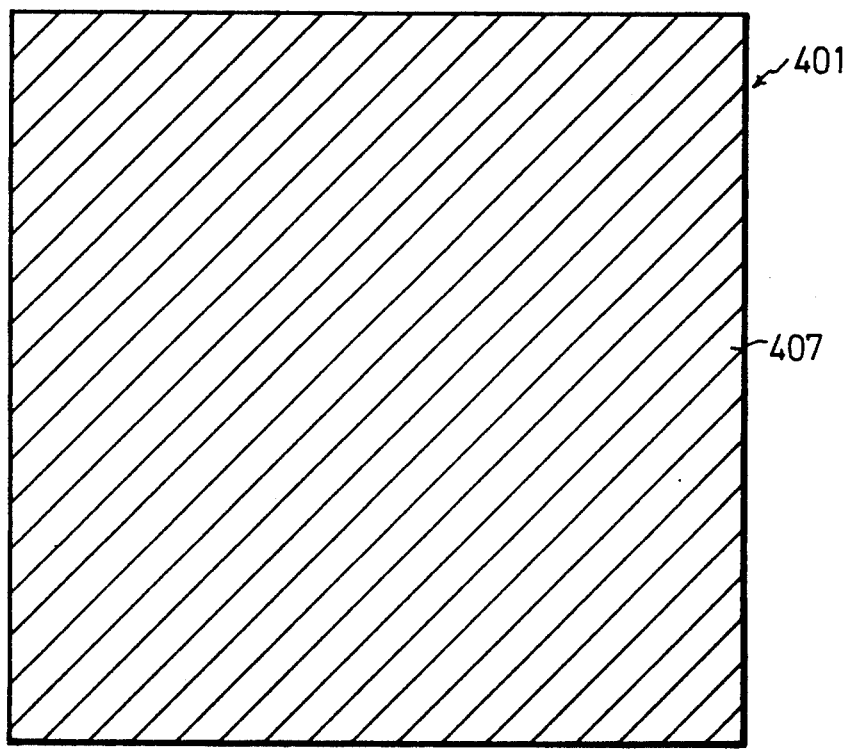
Figure 6E:
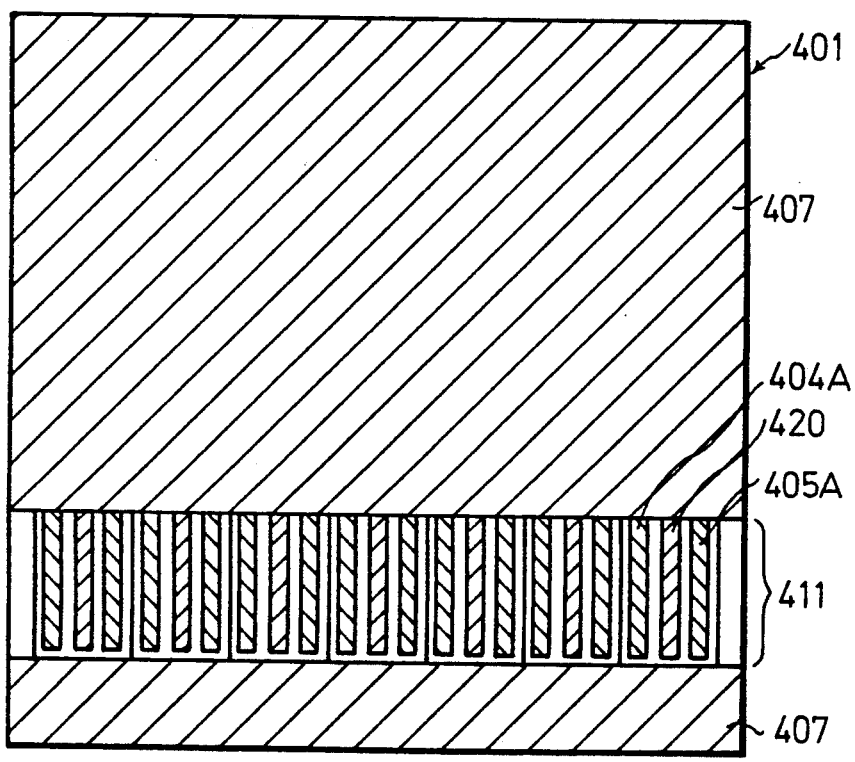
Figure 6F:
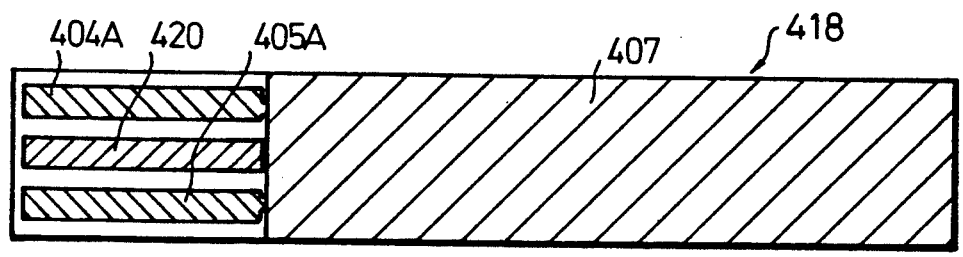
Figure 7A:
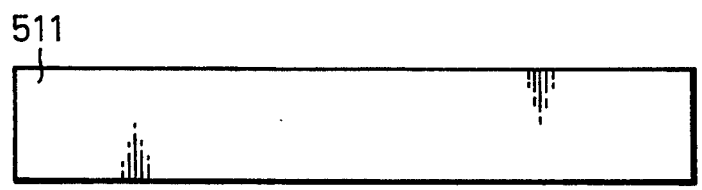
FIGS. 7(a) through (l) show a process sequence according to the present invention, in sectional and plan views.
Figure 7B:
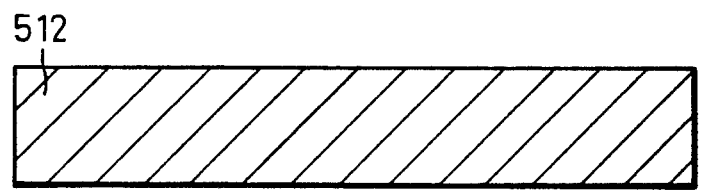
Figure 7C:
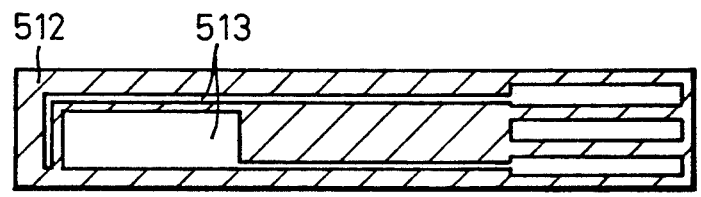
Figure 7D:
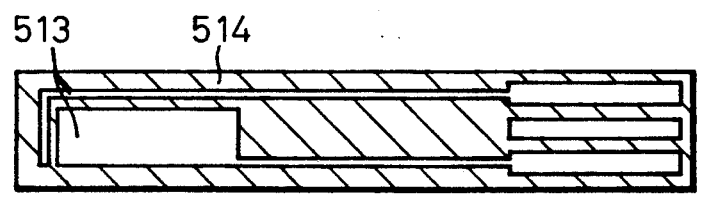
Figure 7E:
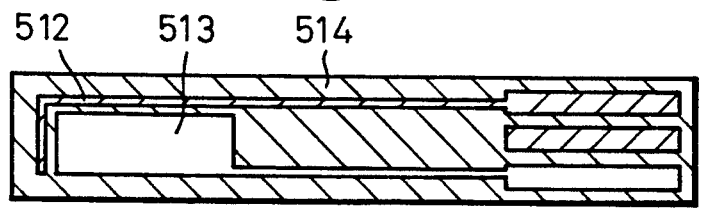
Figure 7F:
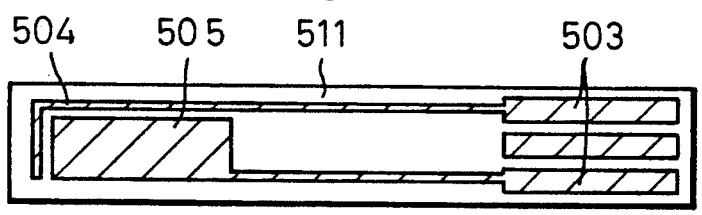
Figure 7G:
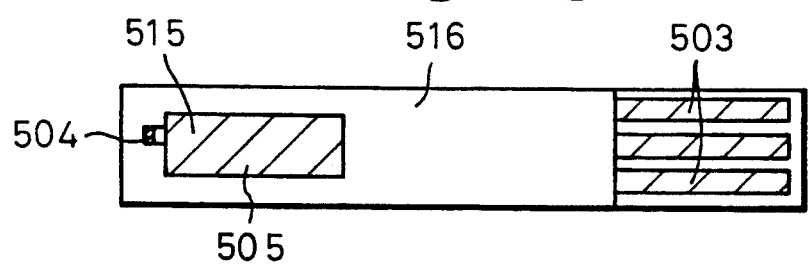
Figure 7H:
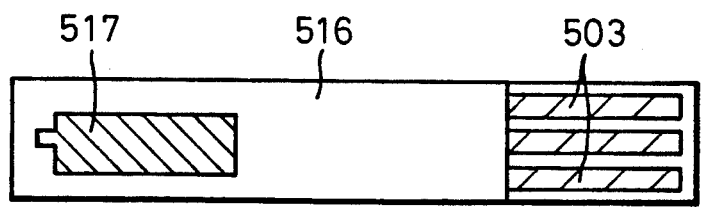
Figure 7I:
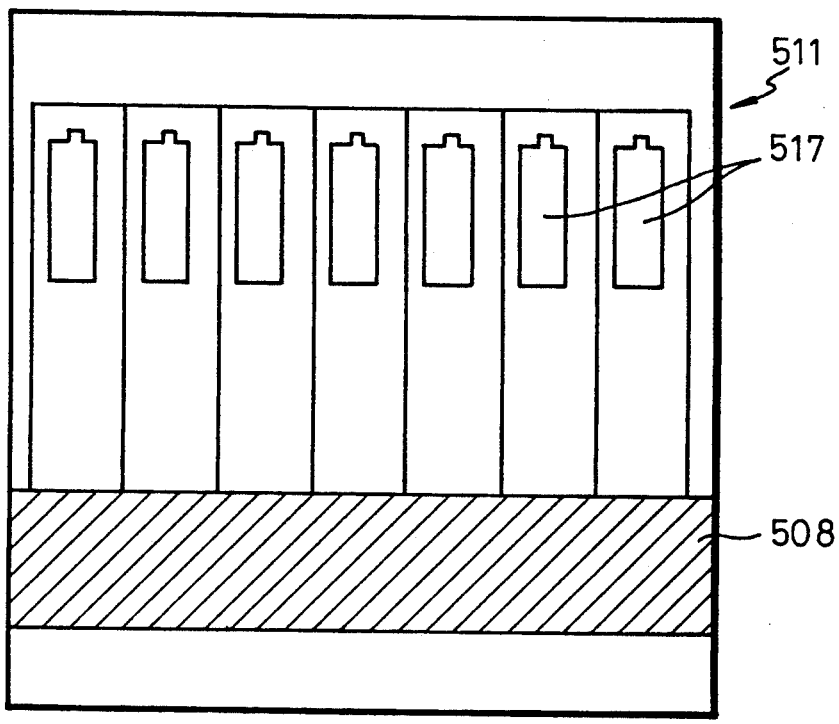
Figure 7J:
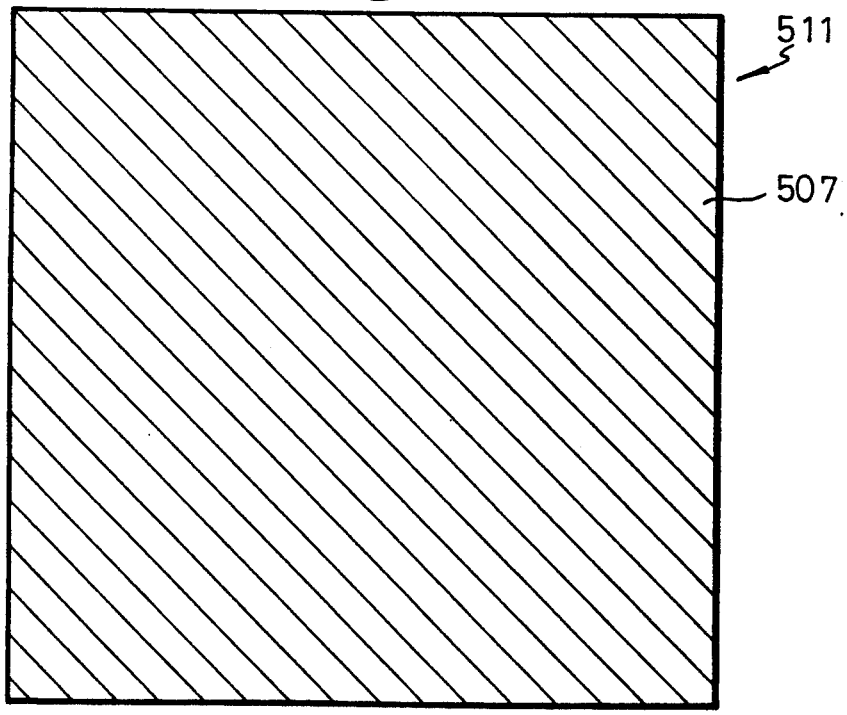
Figure 7K:
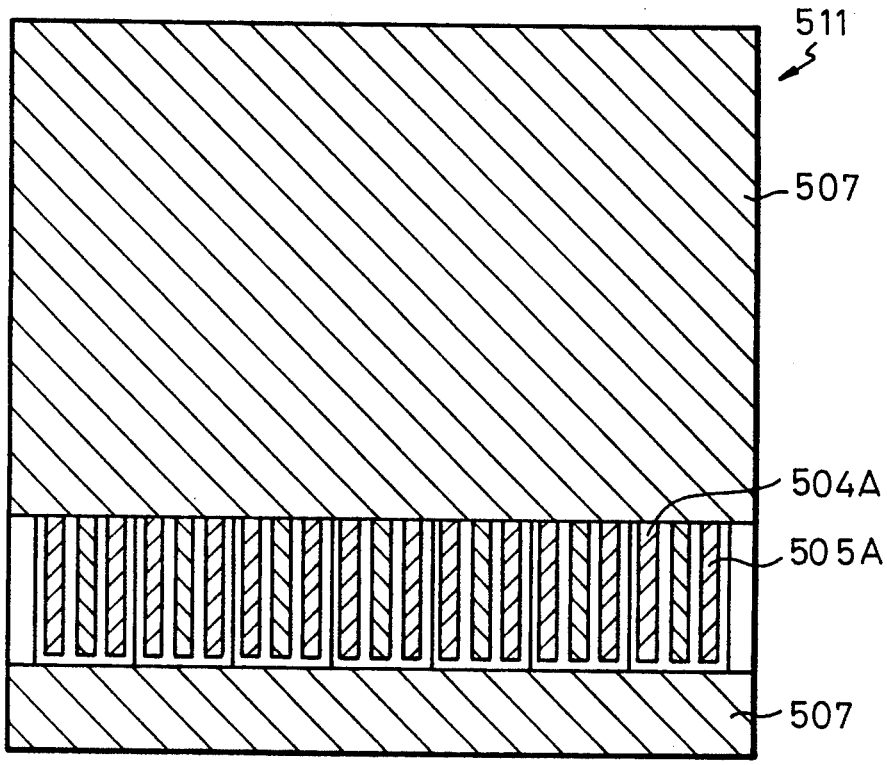
Figure 7L:
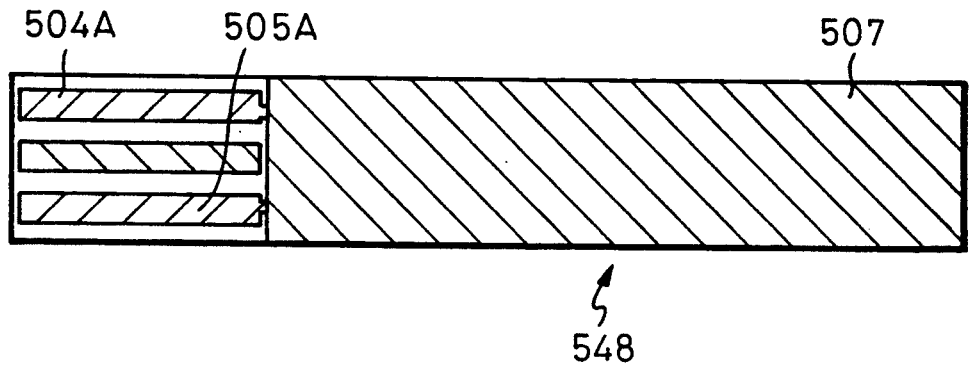

FIG. 5 shows a calibration curve obtained in this case, from which it is seen that a good linearity is ensured over the entire range of the dissolved oxygen concentration of from 0 ppm through 8 ppm, i.e., the saturation concentration.

Example 3

Referring to FIG. 6, a process sequence for producing a miniaturized oxygen electrode according to the present invention by using an electrically insulating flat substrate other than a silicon wafer will be described.

Step 1: Forming Component Electrode Pattern (FIG. 6(a))

A 60 mm square, 1.6 mm thick, cleaned electrically insulating flat substrate 401 was prepared. The insulating substrate 401 may be made of glass, quartz, ceramics, plastics or other electrically insulating substances.

A component electrode pattern consisting of an anode 404 and a cathode 405 was formed on the insulating substrate 401 by either of the following procedures (a) and (b): (a) A silver thin layer is formed by vacuum deposition and is etched to form a predetermined electrode pattern, in the same manner as used in preceding Examples 1 and 2.

(b) An electroconductive paste (Fujikura Kasei Co., D-1230 modified) is screen-printed on the substrate.

The component electrodes 404 and 405 have ends for external electrical connections or pads 404A and 405A, respectively.

An auxiliary pad 420 provided between the pads 404A and 405A can be used for a miniaturized oxygen electrode having a three-pole structure, for example.

Step 2: Screen-Printing Electrolyte Composition (FIG. 6(b))

The same electrolyte composition as used in Example 1 was screen-printed to fill a region 409 of the oxygen sensing site, and thereby form an electrolyte-containing material 406.

Step 3: Forming Pad Region Cover Film (FIG. 6(c))

A thermosetting release coating (Fujikura Kasei Co., XB-801) was screen-printed at a pad region 411 containing the pads 404A and 405A and the auxiliary pad 420, to form a cover film 408 covering the pad region 411.

Step 4: Forming Oxygen Gas-Permeable Membrane (FIG. 6(d))

An oxygen gas-permeable membrane 407 having a double-layered structure was formed on the substrate 401 to entirely cover the upper surface of the substrate 401. The lower and the upper layers of the membrane 407 were formed by applying a negative-type photoresist (Tokyo Ohka Kogyo Co., Ltd., OMR-83, viscosity 100 cP) and a silicone resin (Toray-Dow Corning Silicone Co., SE9176) by spin coating, respectively, and then curing the applied layers.

Step 5: Exposing Pad Region (FIG. 6(e))

The cover film 408 formed on the pad region 411 was peeled with a pincette to selectively remove the oxygen gas-permeable membrane 407 in that portion, and thereby expose the pads 404A and 405A of a miniaturized oxygen electrode. The auxiliary pad 420 was simultaneously exposed.

Step 6: Separating Miniaturized Oxygen Electrodes (FIG. 6(f))

A plurality of miniaturized oxygen electrodes were collectively formed on the electrically insulating substrate 401 at one time by the preceding Steps 1 to 6, and were cut into chips by a dicing saw. The shown example provided seven chips of miniaturized oxygen electrodes 418 from a single substrate, simultaneously.

Although the preceding Examples formed the component electrodes of silver, the component electrodes may be formed of gold instead of silver, or a cathode and an anode may be formed of gold and silver, respectively.

For example, the component electrodes can be formed of gold instead of silver by a partial modification of the process steps of Example 1, as follows.

Example 4

Steps 8 and 10 of Example 1 were modified in the following manner.

In Step 8 (FIGS. 3(g1) and 3(g2)), the same operation was performed as in Example 1, except that a gold thin layer 315 (4000 Å thick) was vacuum deposited instead of the silver thin layer 315 (4000 Å thick).

The subsequent Step 9 (FIGS. 3(h1) and 3(h2)) was performed in the same manner as in Example 1.

In Step 10 (FIGS. 3(i1) and 3(i2)), the same operation was performed as that in Example 1, except that the wafer 301 was immersed in an etchant for gold (KI/4 g + I$_2$/1 g + water/40 ml) instead of the etchant for silver.

These modifications provided a miniaturized oxygen electrode having a component electrode formed of gold.

A miniaturized oxygen electrode having a gold cathode and a silver anode may be produced in the following manner.

Example 5

Referring to FIG. 7, a process sequence for producing a miniaturized oxygen electrode having a gold cathode and a silver anode according to the present invention by using a glass substrate will be described.

Step 1: Cleaning Substrate FIG. 7(a)

A 60 mm square, 1.6 mm thick glass substrate 511 was thoroughly washed with a detergent (for example, Furuuchi Kagaku Co., Semico Clean 56) and acetone.

Step 2: Forming Thin Layers of Chromium, Gold and Silver (FIG. 7(b))

A chromium thin layer (400 Å thick, for example), a gold thin layer (4000 Å, for example) and a silver thin layer 512 (4000 Å thick, for example) were formed on the substrate 511, in that order, by a vacuum deposition. The chromium thin layer ensures a good adhesion between the glass substrate 511 and component electrodes of gold and silver.

Step 3: Forming Photoresist Pattern (FIG. 7(c))

A positive-type photoresist (for example, Tokyo Ohka Kogyo Co., Ltd., OFPR-800, 20 cP or OFPR-5000, 50 cP) was applied on the silver thin layer 512 and prebaked at 80° C. for 30 min. The thus-formed photoresist layer was exposed to light and developed to form a photoresist pattern 513 corresponding to all component electrodes.

Step 4: Etching Gold and Silver Thin Layers FIG. 7(d))

The substrate 511 was immersed in an etchant for silver (for example, 29%NH$_4$OH/1 ml+31%H$_2$O$_2$/ 1 ml+ water/20 ml) to pattern the silver thin layer 512. The substrate 511 was then immersed in an etchant for gold (for example, KI/4 g+I$_2$/1 g+water/40 ml) to pattern the gold thin layer.

This exposed the chromium thin layer 514 in the portion not covered with the photoresist layer.

Step 5: Re-Patterning Photoresist Pattern FIG. 7(e))

The positive-type photoresist layer 513 was exposed to light and developed again so that the photoresist pattern 513 remained only in the portion at which an anode is to be formed, and the other portion of the photoresist pattern 513 was removed to expose the silver thin layer 512.

Step 6: Patterning Component Electrodes (FIG. 7(f))

The substrate 511 was immersed in an etchant for silver to remove the silver thin layer exposed in the preceding Step 5, and thereby expose the underlying gold thin layer, with the result that the gold cathode 504, including part of the extended card edge portion (or pad) 503, and part of a floating card edge portion (or pad), were exposed. The substrate was then immersed in an etchant for chromium (for example, NaOH/0.5 g+K$_3$Fe(CN)$_6$/1 g+water/4 ml) to remove an open portion of the chromium thin layer 514. The substrate was immersed in acetone to entirely remove the photoresist pattern 513, and thereby expose the silver anode 505 including part of the extended card edge portion (or pad) 503.

This completed the formation of the entire arrangement of component electrodes including the gold cathode 504 and the silver anode 505.

Step 7: Forming Photoresist Pattern FIG. 7(g))

A negative-type photoresist (for example, Tokyo Ohka Kogyo Co., Ltd., OMR-83, 60 cP) was applied to the entire upper surface of the substrate 511 by spin coating and prebaked at 70°-80° C. for 30 min. After an exposure to light and development, the photoresist was postbaked at 150° C. for 30 min. to form a photoresist pattern 516, which covered the substrate surface except for an oxygen sensing site of the silver anode 505, part of the gold cathode 504, and the card edge portion (or pad) 503.

Step 8: Screen-Printing Electrolyte Composition (FIG. 7(h))

An electrolyte composition of the present invention was screen-printed on the oxygen sensing site 515 defined by the photoresist pattern 516, to form an electrolyte-containing material 517.

Step 9: Forming Pad Region Cover Film FIG. 7(i))

A thermosetting release coating (Fujikura Kasei Co., XB-801) was screen-printed on the pad region (or card edge portion) 503 at a thickness of 100 μm, and then cured by heating at 150° C. for 10 min. to form a cover film 508.

Step 10: Forming Oxygen Gas-Permeable Membrane (FIG. 7(j))

A oxygen gas-permeable membrane 507 having a double-layered structure was formed on the glass substrate 511 to entirely cover the substrate upper surface. The lower layer of the membrane 507 was first formed by spin-coating a negative-type phtoresist (Tokyo Ohka Kogyo Co., Ltd., OMR-83, viscosity 100 cP), prebaking at 80° C. for 30 min., exposing the entire substrate surface to light, and postbaking at 150° C. for 30 min. The upper layer was then formed by spin-coating a silicone resin (Toray-Dow Corning Silicone Co., SE9176) and curing by heating at 70° C. for 30 min. in an oven moistened with the water contained in a Petri dish or a beaker placed in the oven.

Step 11: Exposing Pads (FIG. 7(k))

The cover film 508 formed in the pad region 503 was peeled off with a pincette to selectively remove the oxygen gas-permeable membrane 507 in that portion, and thereby expose the pads (or card edges) 504A and 505A of a miniaturized oxygen electrode.

The selective removal of the oxygen gas-permeable membrane 507 was effected in such a way that, when the cover film 508 was peeled off, the oxygen gas-permeable membrane 507 was cut by the edge of the cover film 508 between the membrane portion positioned on the cover film 508 and the other membrane portion away from the cover film 508.

The portion of oxygen gas-permeable membrane remaining on the glass substrate strongly adhered to the substrate and was not exfoliated by the later treatments, including a water vapor treatment describe later. The oxygen gas-permeable membrane also ensures a high reliability such that it does not fracture when attached to a catheter and used in a medical care, or when used for monitoring the oxygen concentration in a fermenter subjected to a sterilization at a temperature of 120° C. and a differential pressure of 1.2 atm. for about 15 min.

Step 12: Separating Miniaturized Oxygen Electrodes (FIG. 7(l))

A plurality of miniaturized oxygen electrodes were collectively formed on the glass substrate 511 at one time and were cut into chips by a dicing saw. The shown example provides seven miniaturized oxygen electrodes from a single substrate at one time.

The oxygen gas-permeable membrane strongly adhered to the substrate and did not exfoliate during a cutting thereof along a scribe line, and further, did not exhibit a lowered reliability when subjected to a reliability test.

The miniaturized oxygen electrode according to the present invention can be applied to any clark type device for electrochemically detecting oxygen, including Galvani type, and three-pole type oxygen electrodes.

Figure 8A:
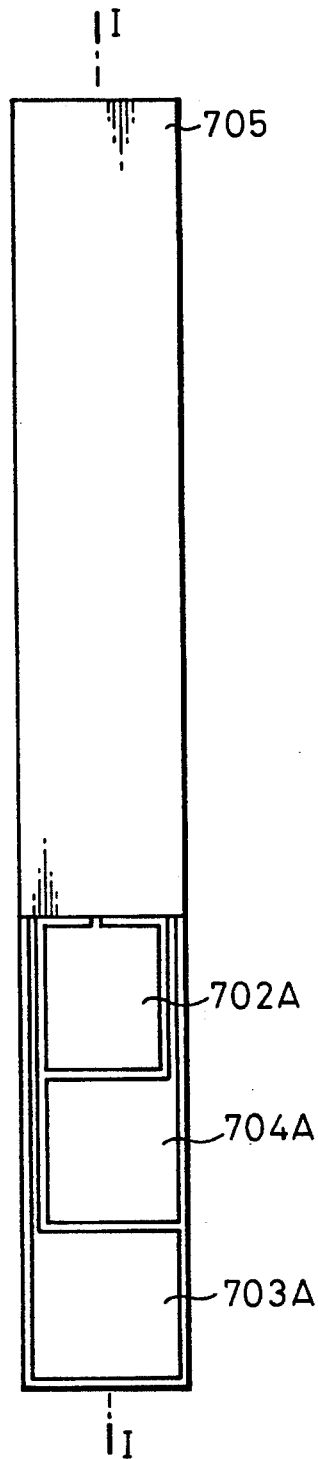
FIGS. 8(a) through (c) show a three-pole miniaturized oxygen electrode.
Figure 8B:
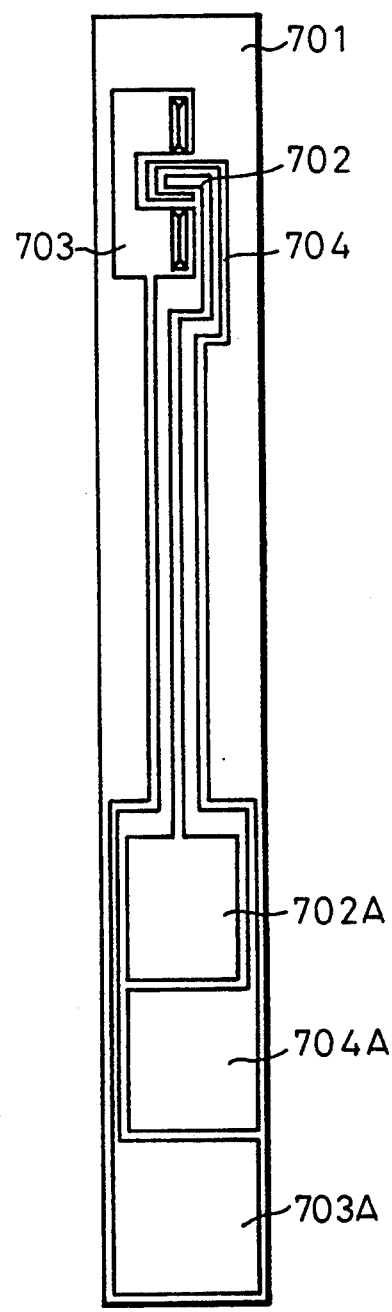

FIGS. 8(a), (b) and (c) show an example of the three-pole type miniaturized oxygen electrode, wherein FIG. 8(b) shows an unfinished structure in which an oxygen gas-permeable membrane is not yet formed.

Figure 8C:
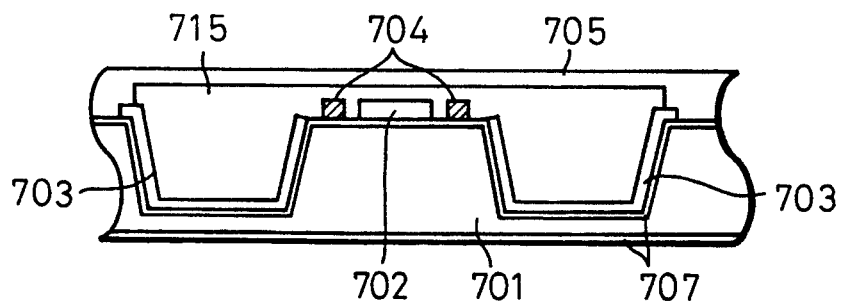

A working electrode 702, a counter electrode 703 and a reference electrode 704 are formed on a silicon wafer 701 (see FIG. 8(b)) and an oxygen gas-permeable membrane 705 covers the surface except for pads 702A, 703A and 704A of the respective electrodes. FIG. 8(c) shows an I—I section of an oxygen sensing site, in which an electrolyte composition 715 is filled in grooves formed in the silicon wafer to form a electrolyte-containing material.

Example 6

A three-pole type miniaturized oxygen electrode according to the present invention and having a basic structure as shown in FIGS. 8(a) to (c) was produced according to the present invention in the following sequence.

Figure 9:
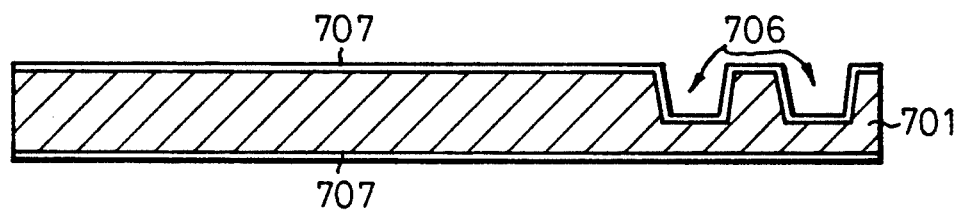
FIGS. 9(a) through (e) show a process sequence for producing a three-pole miniaturized oxygen electrode, according to the present invention, in sectional and plan views.
Figure 9:
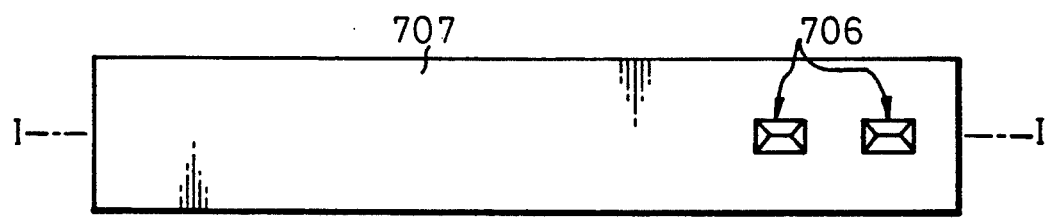
Figure 9:
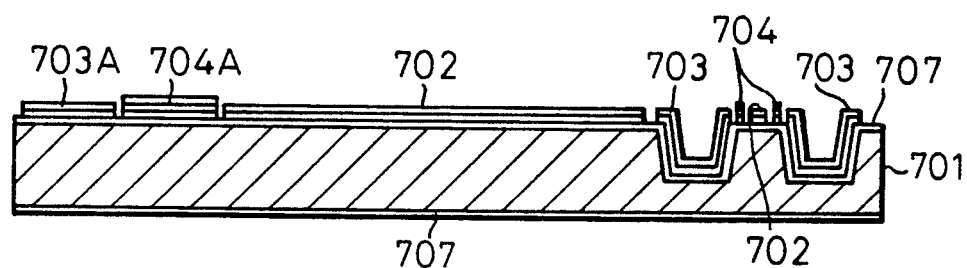
Figure 9:
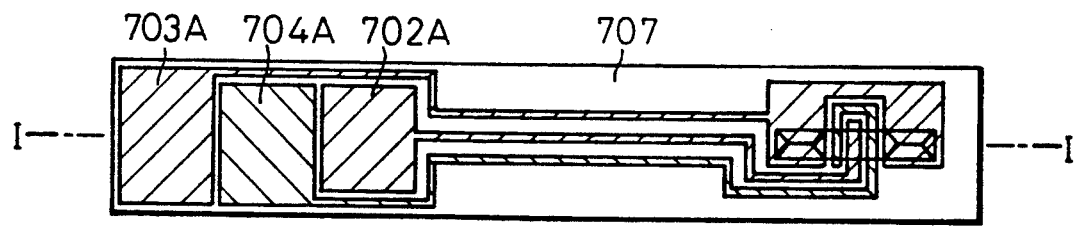
Figure 9:
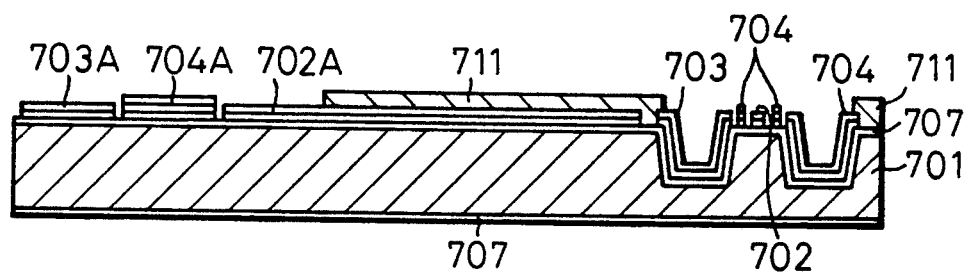
Figure 9:
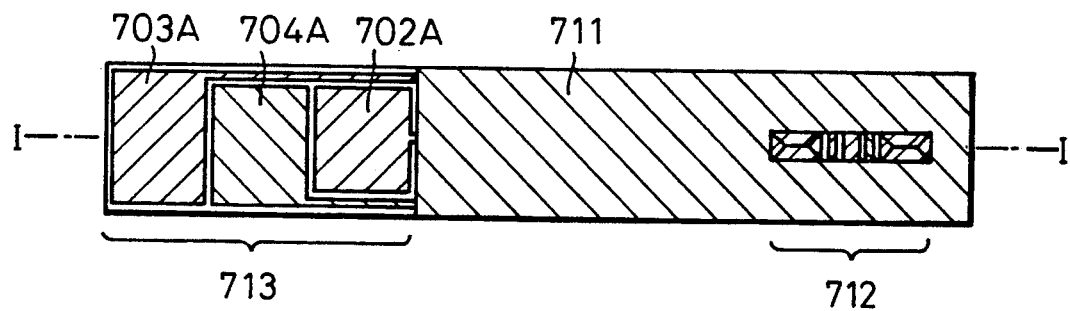
Figure 9:
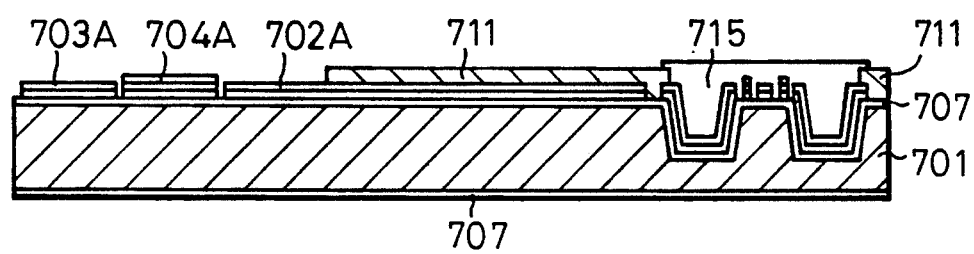
Figure 9:
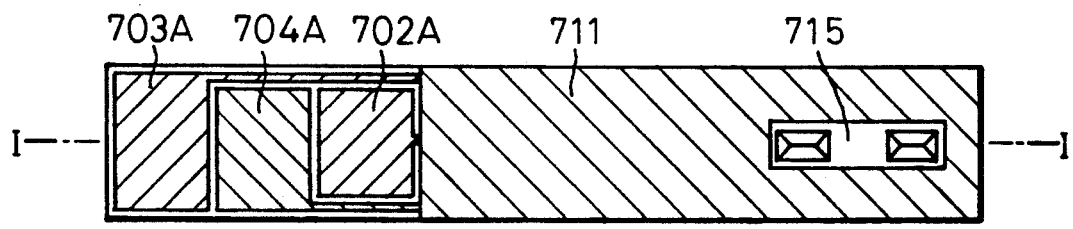
Figure 9:
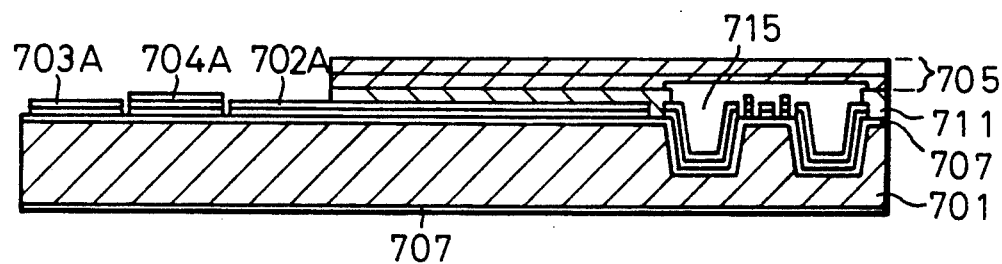
Figure 9:
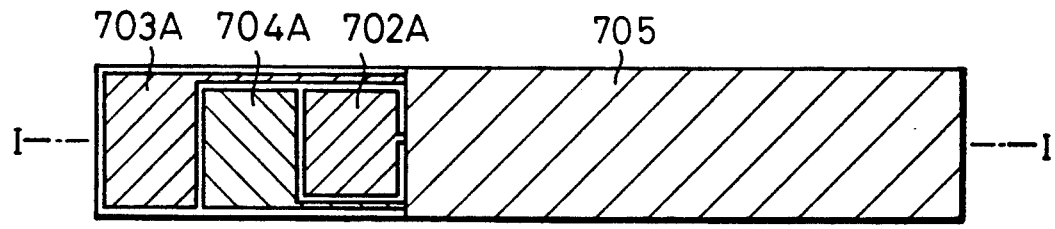

Step 1: Forming Grooves for Receiving Electrolyte-Containing Material (FIGS. 9(a1) and 9(a2))

In the same sequence as carried out in Steps 1 through 7 of Example 1, grooves 706 for receiving an electrolyte-containing material and an $SiO_2$ insulating layer 707 were formed on both sides of a silicon wafer 701.

Step 2: Forming Component Electrode Pattern (FIGS. 9(b1) and 9(b2))

In the same sequence as carried out in Steps 2 through 6 of Example 5, a working electrode 702 and a counter electrode 703, both of gold, and a reference electrode 704 of silver were formed.

Step 3: Forming Photoresist Pattern (FIGS. 9(c1) and 9(c2))

By the same operation as carried out in Step 11 of Example 1, a photoresist pattern 711 was formed to cover the substrate surface except for a region 712 of the oxygen sensing site and a pad region 713.

Step 4: Screen-Printing Electrolyte Composition (FIGS. 9(d1) and 9(d2))

By the same operation carried out in Step 12 of Example 1, an electrolyte composition 715 was screen-printed on the oxygen sensing site 712.

Step 5: Forming Pad Region Cover Film (not shown)

By the same operation as carried out in Step 13 of Example 1, a removable cover film was formed.

Step 6: Forming Oxygen Gas-Permeable Membrane (not shown)

By the same operation as carried out in Step 14 of Example 1, an oxygen gas-permeable membrane was formed.

Step 7: Exposing Pads (FIGS. 9(e1) and 9(e2))

By the same operation as carried out in Step 15 of Example 1, pads 702A, 703A and 704A were exposed.

Step 8: Separating Miniaturized Oxygen Electrodes not shown)

By the same operation as carried out in Step 16 of Example 1, a number of miniaturized oxygen electrode formed on the silicon wafer were cut into chips.

In Examples 1 through 6, miniaturized oxygen electrodes were produced at a yield of 98% or more and exhibited a good response characteristic, i.e., an output fluctuation of less than ±3% when measured in water saturated with oxygen.

The produced miniaturized oxygen electrode is preserved in the dried condition and can be made operative when supplied with water through the oxygen gas-permeable membrane by water vapor sterilization (for example, at 121° C. and 2.2 atm.), immersion in water, exposure to a saturated water vapor, etc.

Figure 10:
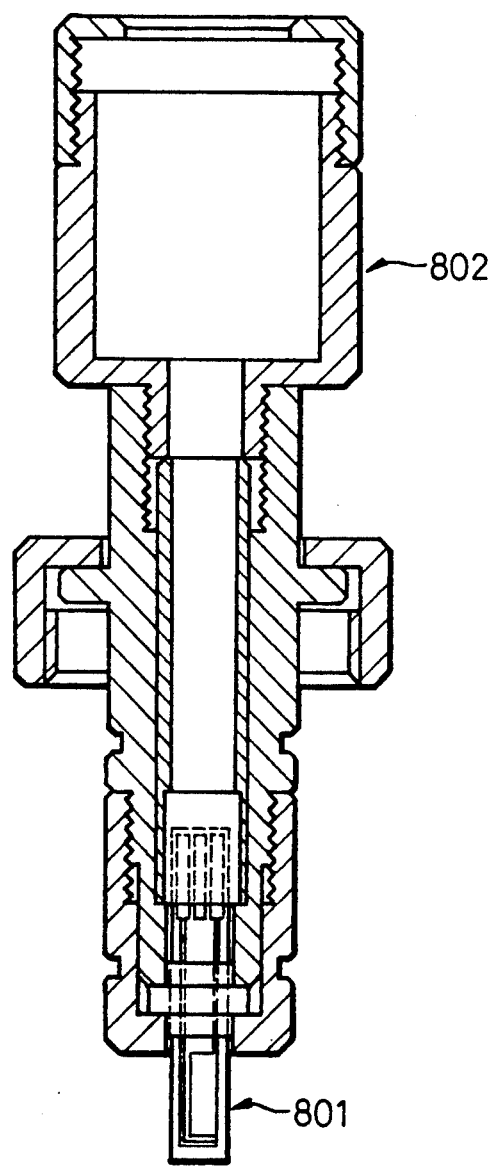
FIG. 10 shows a miniaturized oxygen electrode mounted on an adapter for use in a fermenter, in sectional view.

When an miniaturized oxygen electrode is used for a fermenter, the above-mentioned preparation or water supply may be conveniently effected together with sterilization of the culture medium. As shown in FIG. 10, a miniaturized oxygen electrode 801 of the present invention is conveniently attached to a special adaptor 802 designed for a fermenter (proposed by the present inventors and others in Japanese Patent Application No. 1-231,708).

The external electrical connection of a miniaturized oxygen electrode is usually carried out by inserting the card edge portion (or pad portion) 503 to a card edge connecter (for example, Fujitsu Ltd., Type 760).

Figure 11:
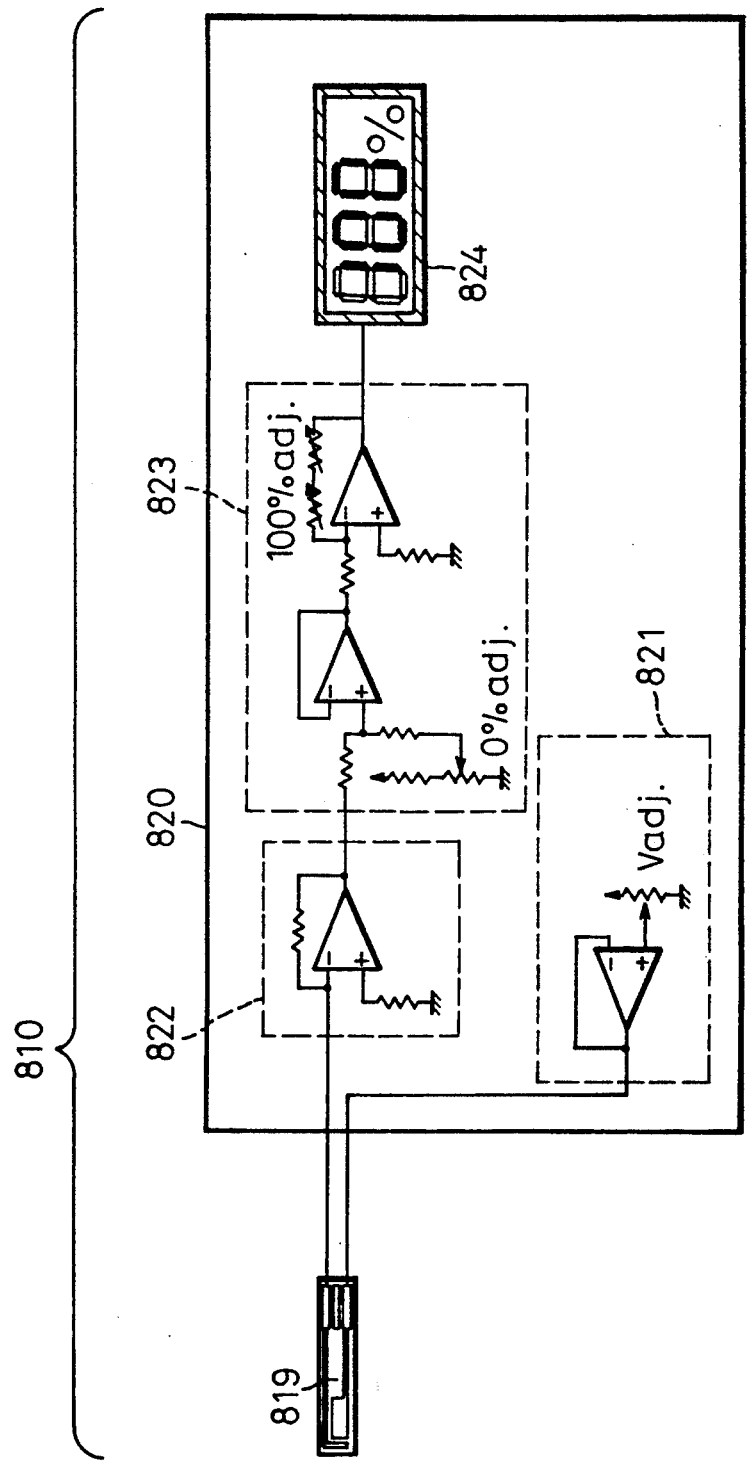
FIG. 11 shows an arrangement of a device for measuring the oxygen concentration in which a miniaturized oxygen electrode according to the present invention is applied.

FIG. 11 shows an arrangement of an oxygen concentration measuring device in which a miniaturized oxygen electrode of the present invention is used. An oxygen concentration measuring device 810 is composed of a miniaturized oxygen electrode 819 of the present invention and a controller 820. The controller 820 is composed of a voltage supply unit 821 for generating a voltage to be supplied to the oxygen electrode 819, a current-to-voltage converter unit 822 for converting an output current from the oxygen electrode 819 to a voltage, a calibration unit 823 for calibrating an output voltage from the converter unit 822 at the oxygen concentrations of 0% and 100%, and a display unit 824. The device 810 measures the dissolved oxygen concentration in many kinds of solutions and the oxygen concentration of gas phases.

As herein described, the present invention provides a miniaturized oxygen electrode which can be massproduced at a high efficiency by collectively and uniformly processing a substrate as a whole by using the semiconductor process, a production process thereof, and an electrolyte composition able to be advantageously used therefor.

Example 7

Figure 12A:
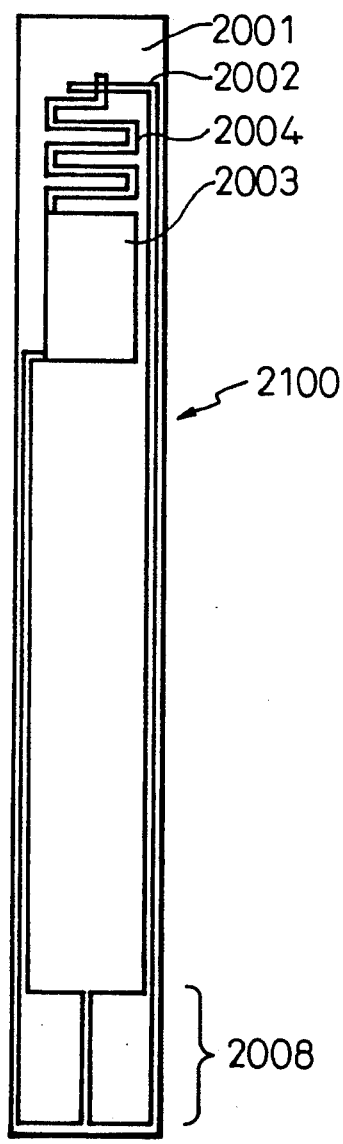
FIGS. 12A and 12B show arrangements of miniaturized oxygen electrodes according to the present invention, having two-pole and three-pole type structures, respectively.
Figure 12B:
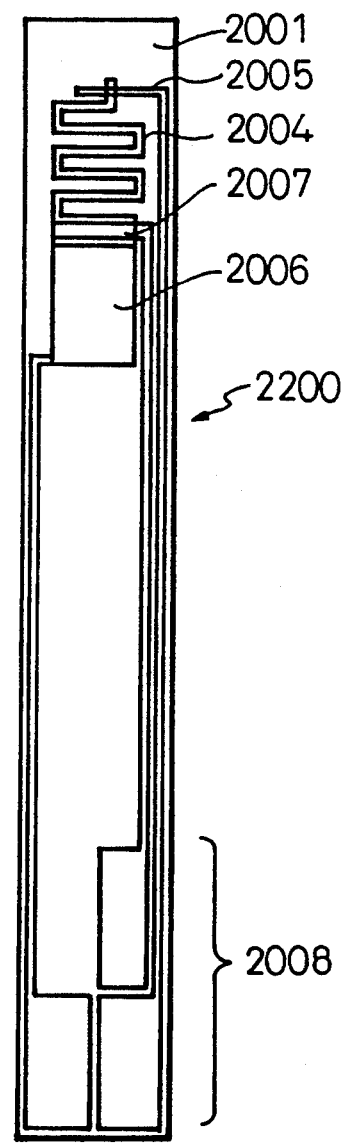

FIGS. 12A and 12B exemplify miniaturized oxygen electrodes of two- and three-pole types according to the present invention, respectively, in which an oxygen gas-permeable membrane is omitted for depicting the inside arrangement.

Referring to FIG. 12A, a two-pole type miniaturized oxygen electrode 2100 has a set of component electrodes composed of a cathode 2002 and an anode 2003 which are disposed on an electrically insulating substrate 2001, and an elongated, slender, serpentine electrolyte-containing material 2004 connecting the cathode 2002 and the anode 2003. Application of voltage to the component electrodes 2002 and 2003 and measuring current output therefrom can be effected through a pad region 2008 for external electrical connection. A gas-permeable membrane, omitted from the figure, covers the shown area other than the pad region 2008.

Referring to FIG. 12B, a three-pole type miniaturized oxygen electrode 2200 has a set of component electrodes composed of working, counter and reference electrodes 2005, 2006 and 2007, respectively, which are disposed on an electrically insulating substrate 2001, the working electrode 2005 being interconnected with the counter and reference electrodes 2006 and 2007 through an elongated, slender, serpentine electrolyte-containing material 2004. Application of voltage to these component electrodes and measuring current output therefrom can be effected through a pad region 2008 for external electrical connection. A gas-permeable membrane, omitted from the figure, covers the shown area other than the pad region 2008.

A silicon wafer is used as the electrically insulating substrate 2001 and the component electrodes are formed by using a process for producing semiconductor devices. The electrolyte-containing material 2004 is formed by printing a composition containing the electrolyte on the substrate 2001.

Example 8

FIGS. 13A and 13B show another example of a two-pole type miniaturized oxygen electrode according to the present invention, in a complete form (FIG. 13A) and in a forth in which a gas-permeable membrane is omitted for depicting the inside arrangement (FIG. 13B), respectively.

Referring to FIGS. 13A and 13B, a two-pole type miniaturized oxygen electrode 3100 has a silicon wafer 3001 on which disposed are a cathode 3002, an anode 3003 and an elongated electrolyte-containing material 3004 in the form of an inverted "L" connecting the cathode 3002 and the anode 3003. Voltage application to the component electrodes 3002 and 3003 and measuring current output therefrom can be effected through a pad region 3008 for external electrical connection. A gas-permeable membrane 3009 covers the shown area other than the pad region 3008.

The miniaturized oxygen electrode 3100 is preferably produced by a process in the sequence shown by FIGS. 14A through 14I in (a) plan view and (b) sectional view along the line I—I of (a).

For simplicity in the following explanation, the process sequence is described for a single chip of a miniaturized oxygen electrode. In the actual manufacturing process, however, multiple miniaturized oxygen electrodes are formed simultaneously on a single silicon wafer. Details of an electrolyte-containing material and a pad region cover film are disclosed in Japanese Patent Application No. 4-32120 and are not herein duplicated.

Step 1

A 400 μm thick, (100) plane silicon wafer 4001 is cleaned by a mixture of hydrogen peroxide and ammonia and then by a concentrated nitric acid.

Step 2 (see FIGS. 14A(a) and 14A(b))

The cleaned wafer 4001 is subjected to thermal oxidation at 1000° C. for 200 min to form a 0.8 μm thick $SiO_2$ insulating layer 4002 on both sides thereof.

Step 3 (see FIGS. 14B(a) and 14B(b))

On one side of the wafer 4001, a 400 Å thick chromium film 4003, a 1000 Å thick nickel film 4004, and a 5000 Å thick silver film 4005 are formed in that order by vacuum deposition.

Figure 14C:
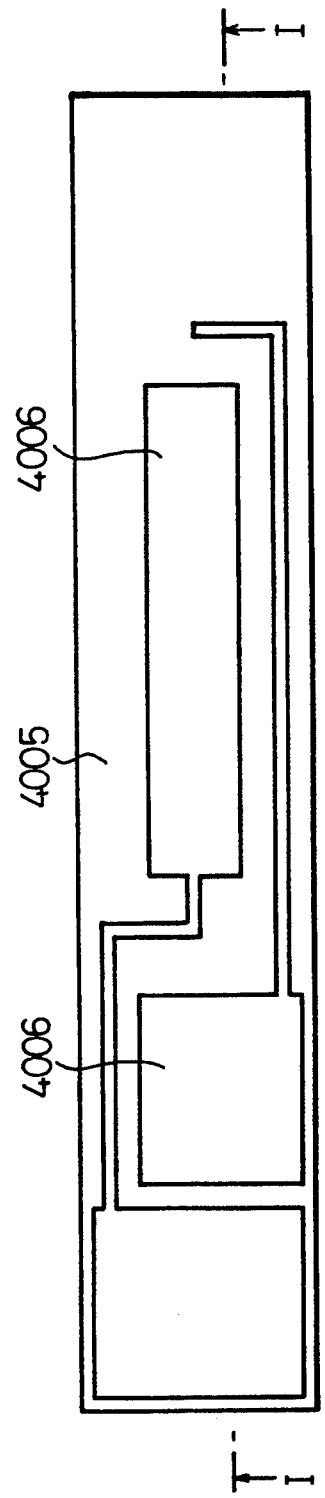
Figure 14C:
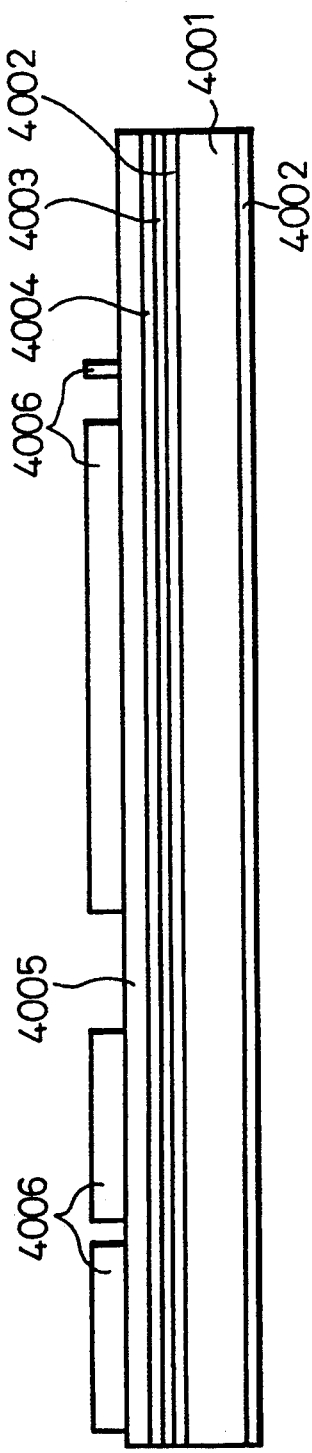

Step 4 (see FIGS. 14C(a) and 14C(b))

A positive-type photoresist (Tokyo Ohka Kogyo Co., Ltd., OFPR-800) is applied on the wafer 4001 by spin coating, prebaked at 80° C. for 30 min, exposed to light and developed to form a photoresist pattern 4006 as an etching mask.

Step 5 (see FIGS. 14D(a) and 14D(b))

The silver film 4005, the nickel film 4004, and the chromium film 4003 are etched with the following etchants, respectively, and the photoresist pattern 4006 is removed by acetone, to form an electrode pattern including a cathode 4007 and an anode 4008.

Etchants for silver: $NH_3$ water (1 ml)+$H_2O_2$ (1 ml) +water (20 ml)

for nickel: 10% ferric chloride aqueous solution for chromium: NaOH (0.5 g)+$K_3Fe(CN)_6$ (1 g)+water (4 ml)

Step 6 see FIGS. 14E(a) and 14E(b))

To cover the area shown in FIG. 14D(a) except for the cathode 4007, the anode 4008 and the pad region 4009, an electrically insulating film 4010 of a negative-type photoresist (Tokyo Ohka Kogyo Co., Ltd., OMR-83) is formed by applying the photoresist on the wafer 4001, prebaking at 80° C. for 30 min, exposing, developing, and postbaking at 150° C. for 30 min.

Figure 14F:
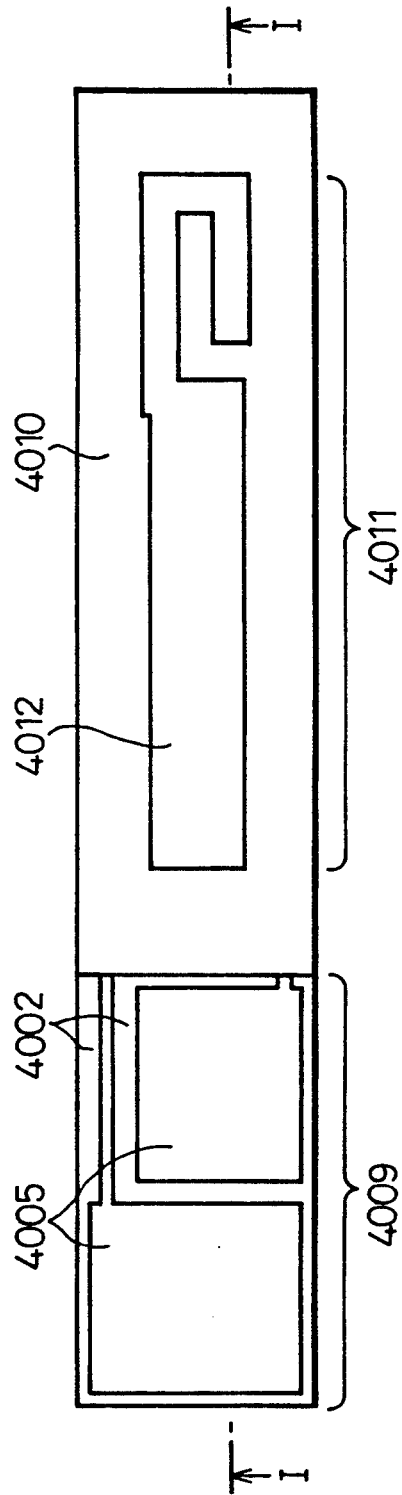
Figure 14F:
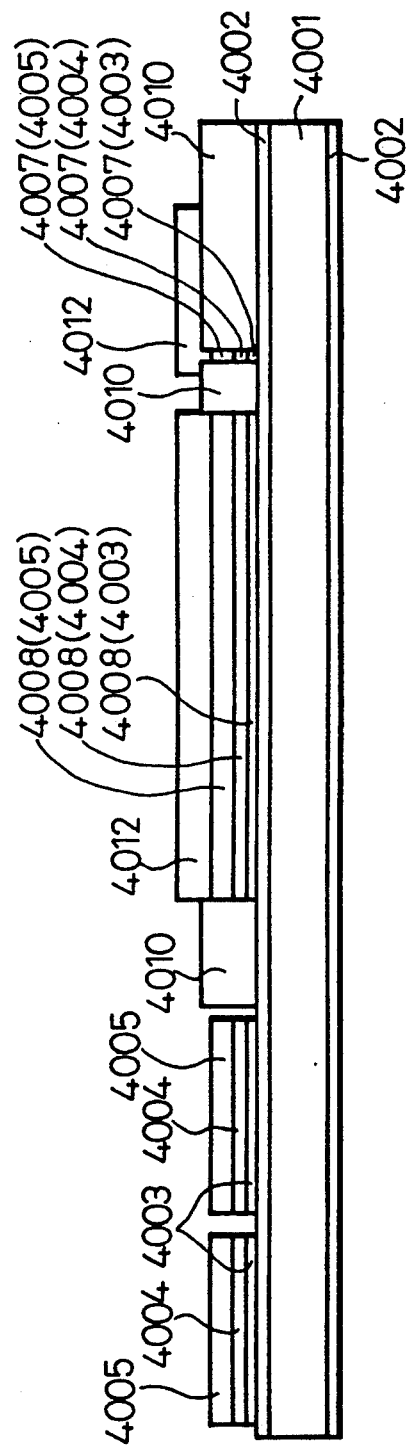

Step 7 (see FIGS. 14F(a) and 14F(b))

An electrolyte composition 4012 is screen-printed on an oxygen-sensing site 4011 which acts as an actual oxygen electrode. The electrolyte composition 4012 can be prepared by dispersing a powdered potassium chloride in an alcoholic solution of polyvinylpyrrolidone.

Step 8 (see FIGS. 14G(a) and 14G(b))

A thermosetting release coating (Fujikura Kasei Co., XB-801) is screen printed on the pad region 4009 at a thickness of 100 μm and is then cured at 150° C. for 10 min to form a pad region cover film 4013.

Step 9 (see FIGS. 14H(a) and 14H(b))

An oxygen gas-permeable membrane 4014 composed of two layers is formed on the wafer 4001 to entirely cover the substrate upper surface. The lower layer 4014L of the membrane 4014 is first formed by spin-coating a negative-type photoresist (Tokyo Ohka Kogyo Co., Ltd., OMR-83), prebaking at 80° C. for 30 min, exposing the entire surface of the wafer 4001 to light, and postbaking at 150° C. for 30 min. The upper layer 4014U of the membrane 4014 is then formed by spin-coating a silicone resin (Toray-Dow Corning Silicone Co., SE9176) and curing at 70° C. for 60 min in an oven moistened with the water contained in a Petri dish or beaker placed in the oven.

Step 10 (see FIGS. 14I(a) and 14I(b))

The cover film 4013 formed in the pad region 4009 is peeled off with a pincette to selectively remove the oxygen gas-permeable membrane 4014 in that portion, and thereby expose the pad region 4009 of a miniaturized oxygen electrode.

Step 11

The multiple miniaturized oxygen electrodes 4015 formed on a single silicon wafer 4001 are cut into chips by a dicing saw.

FIGS. 15A and 15B show another example of a three-pole type miniaturized oxygen electrode according to the present invention, in a complete form (FIG. 15A) and in a form in which a gas-permeable membrane is omitted for depicting the inside arrangement (FIG. 15B), respectively.

Referring to FIGS. 15A and 15B, a three-pole type miniaturized oxygen electrode 5100 has a silicon wafer 5001 on which disposed are a set of component electrodes of a working electrode 5002, a counter electrode 5003 and a reference electrode 5004 and an elongated electrolyte-containing material 5005 in the form of an inverted "L" connecting the working electrode 5002 with the counter and reference electrodes 5003 and 5004. Application of voltage to the component electrodes 5002, 5003 and 5004 and measuring current output therefrom can be effected through a pad region 5007 for external electrical connection. A gas-permeable membrane 5006 covers the shown area other than the pad region 5007.

The three-pole type miniaturized oxygen electrode 5100 is produced by substantially the same process sequence as described in Example 8.

Example 10

Figure 16A:
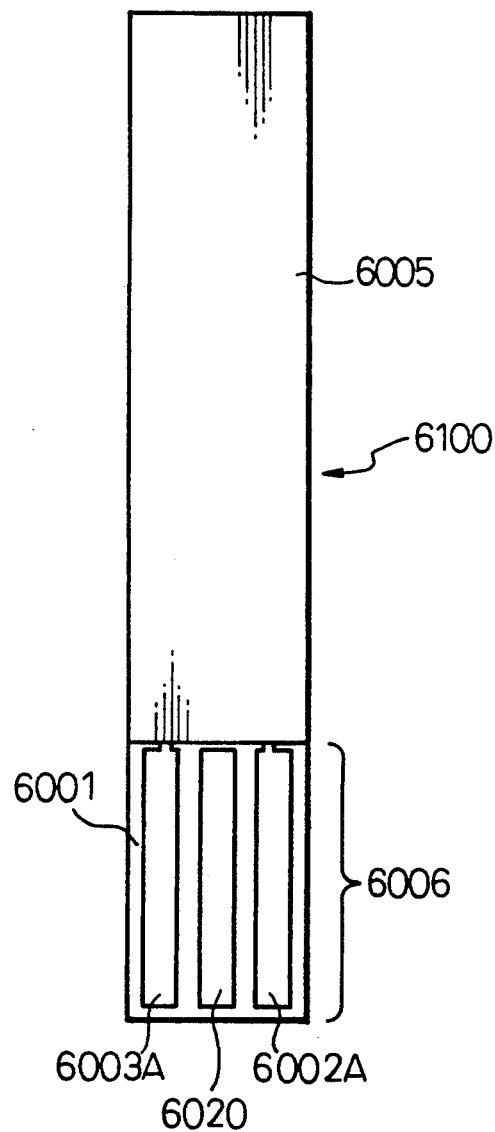
FIGS. 16A and 16B show an arrangement of a two-pole type miniaturized oxygen electrode formed on a glass plate according to the present invention, in a complete form and a form in which a gas-permeable membrane is omitted for depicting the inside arrangement, respectively.
Figure 16B:
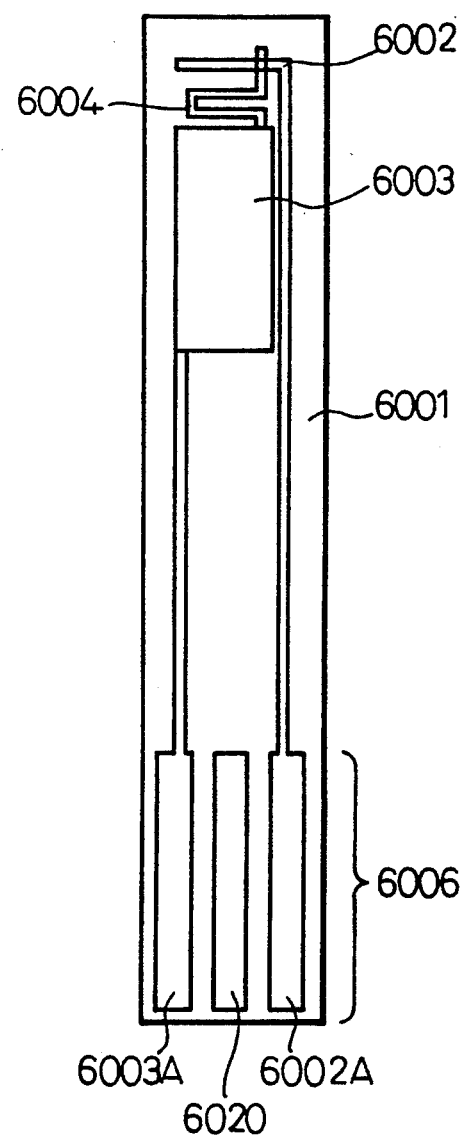

FIGS. 16A and 16B show another example of a two-pole type miniaturized oxygen electrode according to the present invention, in a complete form (FIG. 16A) and in a form in which a gas-permeable membrane is omitted for depicting the inside arrangement (FIG. 16B), respectively.

Referring to FIGS. 16A and 16B, a two-pole type miniaturized oxygen electrode 6100 has a glass substrate 6001 on which are disposed a cathode 6002, an anode 6003 and an elongated, slender, meandering electrolyte-containing material 6004 connecting the cathode 6002 and the anode 6003. Application of voltage to the component electrodes 6002 and 6003 and measuring current output therefrom can be effected through a pad region 6006 for external electrical connection. A gas-permeable membrane 6005 covers the shown area other than the pad region 6006. The symbols 6002A and 6003A denote pad portions of the cathode 6002 and the anode 6003, respectively. An auxiliary pad 6020 provided between the bads 6002A and 6003A can be used for a miniaturized oxygen electrode having a three-pole structure, for example.

The miniaturized oxygen electrode 6100 is preferably produced by a process in the sequence shown by FIGS. 17A through 17E in (a) a plan view and (b) a sectional view along the line I—I of (a).

For simplicity in the following explanation, the process sequence is described for a single chip of miniaturized oxygen electrode. In the actual manufacturing process, however, multiple miniaturized oxygen electrodes are formed simultaneously on a single glass substrate.

Step 1

A 1.6 mm thick, cleaned glass plate 7001 is prepared.

Figure 17A:
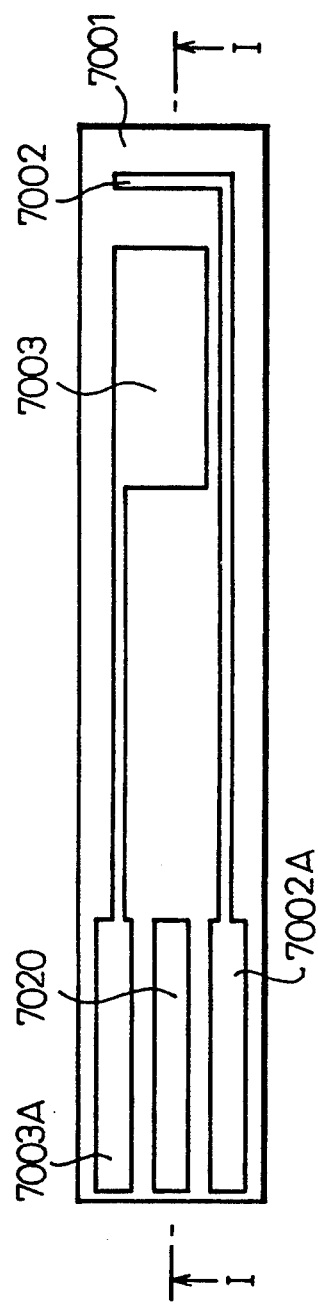
Figure 17A:
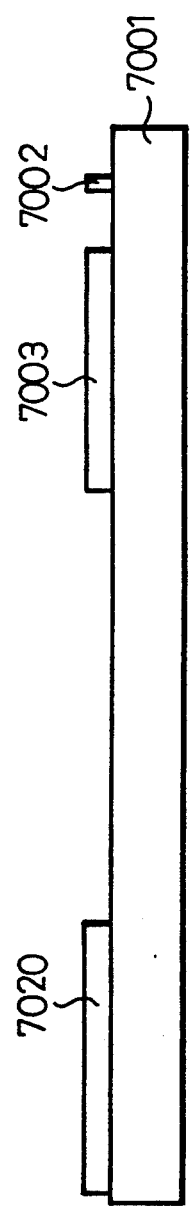

Step 2 (see FIGS. 17A(a) and 17A(b)

A silver paste (Fujikura Kasei Co., D-1230 Modified) is screen-printed on the glass substrate 7001 and fired at 600° C. to form an electrode pattern including a cathode 7002 and an anode 7003. The cathode 7002 and the anode 7003 have pad portions 7002A and 7003A, respectively. An auxiliary pad 7020 is simultaneously printed for a three-pole structure.

Step 3 (see FIGS. 17B(a) and 17B(b))

The same electrolyte composition 7005 as used in Example 2 is screen-printed on an oxygen-sensing site 7004 which act as the actual oxygen electrode.

Step 4 (see FIGS. 17C(a) and 17C(b))

A thermosetting release coating (Fujikura Kasei Co., XB-801) is screen-printed on pad region 7007 and is cured by heating at 150° C. for 10 min to form a pad region cover film 7006.

Step 5 (see FIGS. 17D(a) and 17D(b))

An oxygen gas-permeable membrane 7008 is formed on the entire surface of substrate by spin-coating a silicone resin (Toray-Dow Corning Silicone Co., SE9176) on the substrate 7001 and curing it by heating at 70° C. for 60 min in an oven moistened with the water contained in a Petri dish or beaker placed in the oven.

Figure 17E:
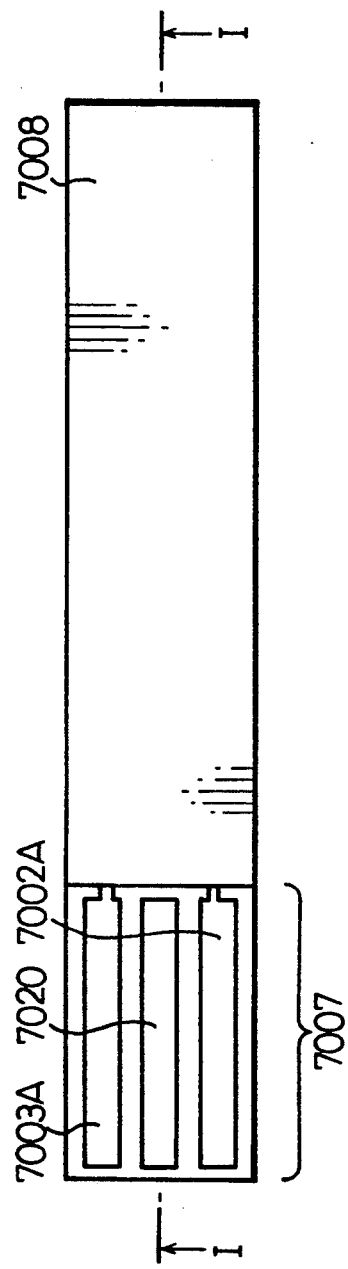
Figure 17E:
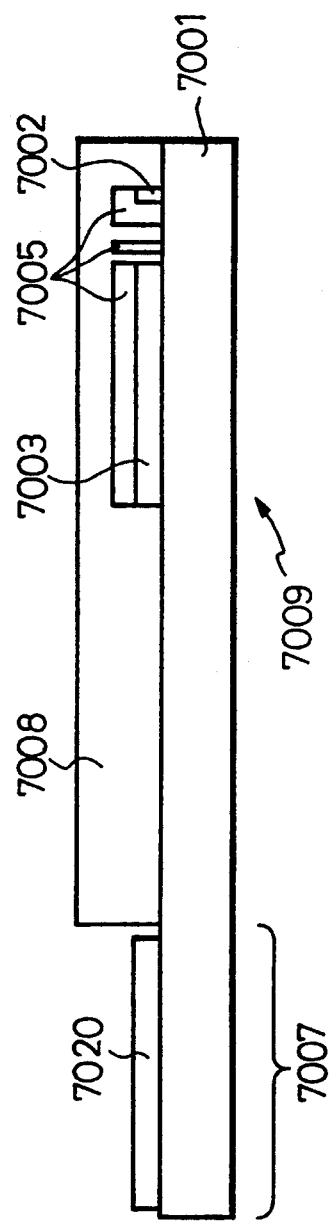

Step 6 (see FIGS. 17E(a) and 17E(b))

The cover film 7006 formed on the pad region 7007 is peeled off by a pincette to selectively remove the oxygen gas-permeable membrane 7008 in that portion to expose the pad region 7007 of a miniaturized oxygen electrode.

Step 7

Multiple miniaturized oxygen electrodes 7009 formed on a single glass substrate 7001 are cut into chips by a dicing saw.

The thus-produced miniaturized oxygen electrodes according to the present invention are brought into operating condition by supplying water to the electrolyte-containing material and thereby forming an electrolytic solution. The water is supplied as vapor by either immersing in boiling water or autoclaving at 121° C.

Figure 18:
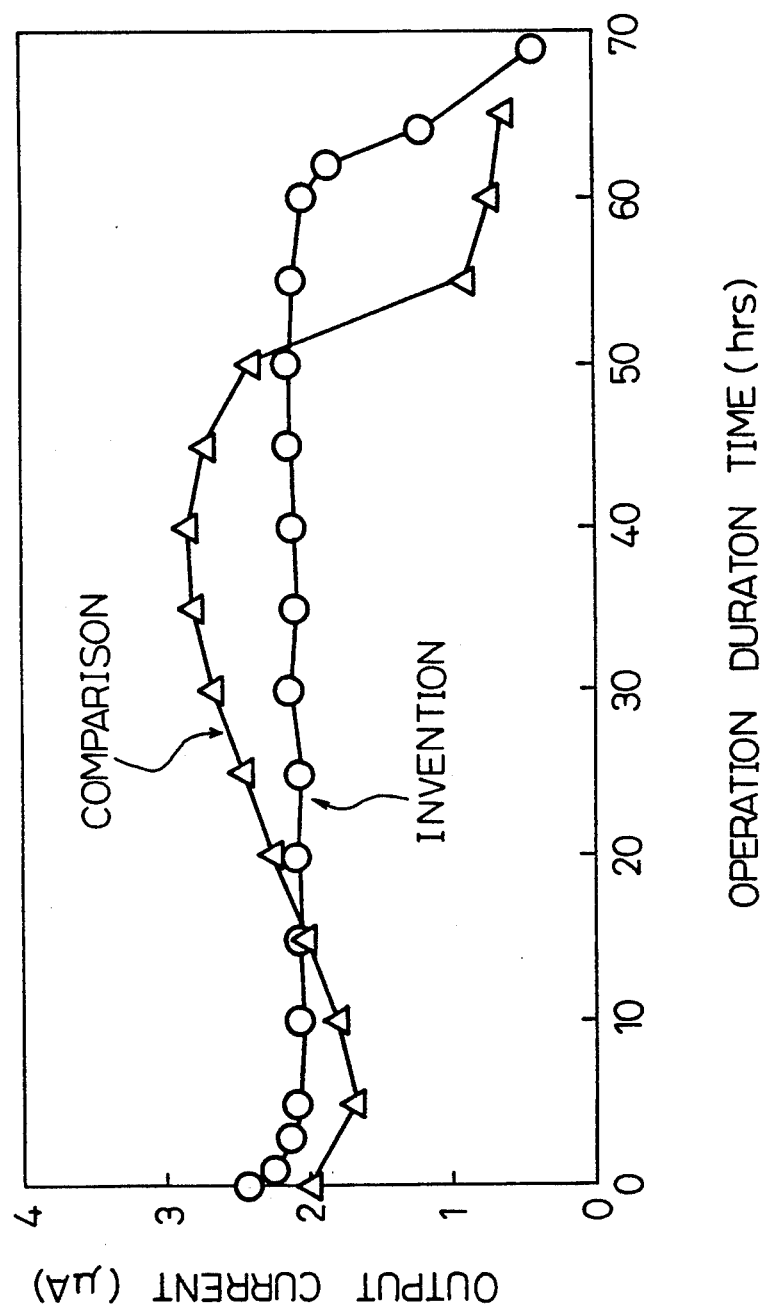
FIG. 18 is a graph showing a relationship between the operation duration time and the output current of a miniaturized oxygen electrode according to the present invention.

FIG. 18 shows a relationship between the operation duration time and the output current of a miniaturized oxygen electrode produced by the above-described process according to the peferred embodiment of the present invention, in comparison with that of a comparative miniaturized oxygen electrode in which the electrolyte-containing material does not have an elongated, slender, zigzag shape such as an inverted "L". It can be seen from FIG. 18 that the comparative miniaturized oxygen electrode cannot provide a stable output current during a long period of continuous operation because of the change of the output current due to the formation of an electroactive substance during the operation, whereas the miniaturized oxygen electrode according to the preferred embodiment of the present invention does provide a stable output current during a long period of continuous operation by virtue of an elongated, slender, zigzag shaped or elongated, slender, inverted "L" shaped electrolyte-containing material.

As hereinabove described, the present invention provides a miniaturized oxygen electrode in which a stable operation over a long period of time is ensured by preventing the reduction reaction of chemical species other than oxygen on a component electrode on which reduction reaction of oxygen alone should occur and also preventing undesirable extra oxidation reactions on the other component electrodes caused by an intermediate product such as $OH^-$ formed on the former component electrode.

We claim:

1. A miniaturized oxygen electrode device comprising:
   an electrically insulating substrate;
   a pair of component electrodes disposed on said insulating substrate;
   an electrolyte-containing material interconnecting said component electrodes,
   one of said pair of component electrodes being an oxygen reducing electrode during operation of said miniaturized oxygen electrode device; and
   an oxygen gas-permeable membrane covering said electrolyte material,
   said electrolyte-containing material having an elongated shape providing a length of material between said component electrodes which is effective for preventing any electroactive substance formed on either of said component electrodes during operation of said oxygen electrode device from diffusing along said material to the other of said component electrodes.

2. A device as set forth in claim 1, wherein one of said component electrodes is a cathode.

3. A device as set forth in claim 1, wherein said one of said pair of component electrodes comprises a working electrode, the other of said pair of electrodes comprises a counter electrode, and said device includes a reference electrode which is connected to said material.

4. A device as set forth in claim 1, wherein said material has an elongated, narrow shape presenting a restricted cross-sectional configuration.

5. A device as set forth in claim 2, wherein said material has an elongated, narrow shape presenting a restricted cross-sectional configuration.

6. A device as set forth in claim 3, wherein said material has an elongated, narrow shape presenting a restricted cross-sectional configuration.

7. A device as set forth in claim 4, wherein said material has an elongated, narrow shape presenting a restricted cross-sectional configuration.

8. A device as set forth in claim 1, wherein said material has a serpentine or meandering shape.

9. A device as set forth in claim 2, wherein said material has a serpentine or meandering shape.

10. A device as set forth in claim 3, wherein said material has a serpentine or meandering shape.

11. A device as set forth in claim 4, wherein said material has a serpentine or meandering shape.

12. A device as set forth in claim 5, wherein said material has a serpentine or meandering shape.

13. A device as set forth in claim 6, wherein said material has a serpentine or meandering shape.

14. A device as set forth in claim 7, wherein said material has a serpentine or meandering shape.

* * * * *

UNITED STATES PATENT AND TRADEMARK OFFICE
CERTIFICATE OF CORRECTION

PATENT NO. : 5,326,450
DATED : July 5, 1994
INVENTOR(S) : AKIO SUGAMA et al.

It is certified that error appears in the above-indentified patent and that said Letters Patent is hereby corrected as shown below:

Column 6, line 68, delete "-".

*Column 15, line 44, "glas" should be --glass--.

*Column 16, line 67, "followings" should be --following--.

Column 17, line 46, after ":" start new paragraph.

*Column 19, line 3, "chlomium" should be --chromium--.

*Column 20, line 6, first "a" should be --An--;

line 50, before "not" insert --(--;

*line 64, "an" should be --a--.

Column 22, lines 24 & 25, "masspro-duced" should be --mass-produced--.

Column 23, line 63, after "6" insert --(--.

Column 24, line 40, insert --Example 9 -- and start new paragraph--.

UNITED STATES PATENT AND TRADEMARK OFFICE
CERTIFICATE OF CORRECTION

PATENT NO. : 5,326,450
DATED : July 5, 1994
INVENTOR(S) : Akio Sugama et al.

It is certified that error appears in the above-indentified patent and that said Letters Patent is hereby corrected as shown below:

*Column 25, line 16, "bads" should be --pads--.

Signed and Sealed this

First Day of November, 1994

Attest:

Attesting Officer

BRUCE LEHMAN

Commissioner of Patents and Trademarks